United States Patent
Teixeira

(10) Patent No.: US 7,277,775 B2
(45) Date of Patent: Oct. 2, 2007

(54) AUTOMATED DYNAMIC PRESSURE-RESPONSIVE DISPENSING SYSTEMS, AND ASSOCIATED METHODS AND COMPUTER PROGRAM PRODUCTS

(75) Inventor: Brian Teixeira, Cary, NC (US)

(73) Assignee: Medi-Physics, Inc., Princeton, NJ (US)

( * ) Notice: Subject to any disclaimer, the term of this patent is extended or adjusted under 35 U.S.C. 154(b) by 262 days.

(21) Appl. No.: 10/625,097

(22) Filed: Jul. 22, 2003

(65) Prior Publication Data

US 2004/0016768 A1    Jan. 29, 2004

(51) Int. Cl.
G06F 17/00    (2006.01)

(52) U.S. Cl. .................. 700/239; 700/240; 222/1; 222/3

(58) Field of Classification Search ............. 700/239, 700/240; 222/1–3
See application file for complete search history.

(56) References Cited

U.S. PATENT DOCUMENTS

| | | | |
|---|---|---|---|
| 4,448,058 A | 5/1984 | Jaffe et al. | |
| 5,427,104 A | 6/1995 | Briend et al. | |
| 5,545,396 A | 8/1996 | Albert et al. | |
| 5,642,625 A | 7/1997 | Cates, Jr. et al. | |
| 5,809,801 A | 9/1998 | Cates, Jr. et al. | |
| 6,079,213 A | 6/2000 | Driehuys et al. | |
| 6,085,743 A | 7/2000 | Rosen et al. | |
| 6,286,319 B1 | 9/2001 | Hasson et al. | |
| 6,295,834 B1 | 10/2001 | Driehuys | |
| 6,318,092 B1 | 11/2001 | Happer et al. | |
| 6,408,849 B1 * | 6/2002 | Spiegelman et al. ... | 128/205.27 |
| 6,942,467 B2 * | 9/2005 | Deninger et al. ......... | 417/313 |
| 2002/0051712 A1 | 5/2002 | Deninger et al. | |

FOREIGN PATENT DOCUMENTS

| | | |
|---|---|---|
| WO | WO99/25243 | 5/1999 |
| WO | WO00/21601 | 4/2000 |

* cited by examiner

*Primary Examiner*—Khoi H. Tran
(74) *Attorney, Agent, or Firm*—Robert F. Chisholm

(57) ABSTRACT

Methods, systems and computer program products for dispensing hyperpolarized gas include or operate a plurality of spaced apart individually operable valves positioned in fluid communication with and located along a gas flow path. The gas flow path that is intermediate the spaced apart valves defines at least one meted holding space with an associated volume that can be selectively isolated from the remainder of the gas flow path. The system and methods include a pressure sensor operably associated with the gas flow path and a control module operably associated with the plurality of spaced apart valves and the pressure sensor, the control module being configured to direct the operational sequence of the opening and closing of the valves, wherein, in operation, the control module directs a plurality of capture and release cycles, the cycles being successively carried out so to temporally isolate a predetermined portion of the gas flow path to capture and then release discrete amounts of gas therein.

10 Claims, 16 Drawing Sheets

AUTOMATED DYNAMIC PRESSURE-RESPONSIVE DISPENSING SYSTEMS, AND ASSOCIATED METHODS AND COMPUTER PROGRAM PRODUCTS

FIELD OF THE INVENTION

The present invention relates to equipment and methods used to remove or dispense hyperpolarized gases. The invention is particularly suitable for dispensing meted quantities of hyperpolarized gases for Magnetic Resonance Imaging ("MRI") or NMR spectroscopy applications.

BACKGROUND OF THE INVENTION

It has been discovered that polarized inert noble gases can produce improved MRI images of certain areas and regions of the body that have heretofore produced less than satisfactory images in this modality. Polarized helium-3 ("$^3$He") and xenon-129 ("$^{129}Xe$") have been found to be particularly suited for this purpose. Unfortunately, as will be discussed further below, the polarized state of the gases is sensitive to handling and environmental conditions and can, undesirably, decay from the polarized state relatively quickly.

Hyperpolarizers are used to produce and accumulate polarized noble gases. Hyperpolarizes artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images or signals of the substance in the body. See U.S. Pat. Nos. 5,545,396; 5,642,625; 5,809,801; 6,079,213, and 6,295,834; the disclosures of these patents are hereby incorporated by reference herein as if recited in full herein.

In order to produce the hyperpolarized gas, the noble gas can be blended with optically pumped alkali metal vapors such as rubidium ("Rb"). These optically pumped metal vapors collide with the nuclei of the noble gas and hyperpolarize the noble gas through a phenomenon known as "spin-exchange." The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (about 10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange."

The alkali metal is removed from the hyperpolarized gas prior to introduction into a patient to form a non-toxic and/or sterile composition. Other polarization techniques not employing alkali metal spin exchange can also be employed as is known to those of skill in the art.

Unfortunately, the hyperpolarized state of the gas can deteriorate or decay relatively quickly and therefore must be handled, collected, transported, and stored carefully. The "$T_1$" decay constant associated with the hyperpolarized gas' longitudinal relaxation time is often used to describe the length of time it takes a gas sample to depolarize in a given situation. The handling of the hyperpolarized gas is critical because of the sensitivity of the hyperpolarized state to environmental and handling factors and the potential for undesirable decay of the gas from its hyperpolarized state prior to the planned end use, i.e., delivery to a patient for imaging. Processing, transporting, and storing the hyperpolarized gases—as well as delivery of the gas to the patient or end user—can expose the hyperpolarized gases to various relaxation mechanisms such as magnetic gradients, contact-induced relaxation, paramagnetic impurities, and the like.

At the time of dispensing the patient dose or bolus (or other point in the production cycle), the quantity of gas actually dispensed into the dose container or bag, the amount of buffer gas or supplemental gas or other fluid desired in the patient formulation of the hyperpolarized gas product, and the polarization level of the hyperpolarized gas itself can vary dose to dose. Therefore, it can be problematic, especially when blending hyperpolarized gas with a buffer gas, to provide reliable repeatable concentrations, quantities, or adjustable hyperpolarized blends of the hyperpolarized gas or gas mixtures over a plurality of doses. In addition, it may be desirable to use different amounts of gas or gas mixtures as well as different sized dose containers, patient to patient.

For example, it may be beneficial to provide different known concentrations of hyperpolarized gases (25%, 50%, and the like) within a relatively constant overall volume of inhalable gas mixture, such as a 1 or 1.5 liter volume (the remainder of the mixture being formed by suitable buffer gases). In other applications, it may be desirable to decide the appropriate formulation in situ, based on the intended use and/or polarization level of the hyperpolarized gas or fluid being dispensed.

Accordingly, there remains a need to provide improved dispensing systems to provide adjustable and/or more reliable concentrations and/or dosages of hyperpolarized gas.

SUMMARY OF THE INVENTION

Embodiments of the present invention provide systems, methods, and computer program products that can automatically dynamically adjust the quantity and/or blend formulation at dispensing in situ.

In certain embodiments, the systems are configured to capture and release discrete serial quantities of two different gases, such as a polarized gas and a buffer gas, and may allow for in situ inputs (user input or measured inputs) to provide adjustable aliquots or allocations of polarized gas and/or buffer gas to generate one or a plurality of the patient-sized product formulations from a multi-bolus sized polarized gas source.

Certain embodiments of the present invention are directed to hyperpolarized gas delivery systems. The systems include: (a) an enclosed gas flow path having a plurality of spaced apart individually operable valves positioned in fluid communication therewith located along the gas flow path, wherein the gas flow path intermediate the spaced apart valves define at least one meted holding space with an associated volume that can be selectively isolated from the remainder of the gas flow path; (b) a pressure sensor operably associated with the gas flow path; and (c) a control module operably associated with the plurality of spaced apart valves and the pressure sensor, the control module being configured to direct the operational sequence of the opening and closing of the valves, wherein, in operation, the control module directs a plurality of capture and release cycles, the cycles being successively carried out so to temporally isolate a predetermined portion of the gas flow path to capture and then release discrete amounts of gas therein.

In particular embodiments, the control module sequentially closes the downstream valve, opens the upstream valve, and then closes the upstream valve to close the meted space to capture a discrete amount of gas in the meted space, and then the control module subsequently opens the downstream valve while the upstream valve is closed to release the discrete amount of gas captured in the meted space so that the discrete amount of gas travels in a predetermined direction downstream of the meted space. The valves may pause for short periods of time between opening and closing (such as less than about 250 ms) during the dispensing cycle.

Other embodiments are directed to hyperpolarized gas production systems. These systems include: (a) an optical pumping cell configured for hyperpolarizing gas via spin-exchange with an optically pumped alkali metal, the optical pumping cell having an associated port and a known volume, wherein, in operation, the optical pumping cell has an associated pressure of above about 1 atm; (b) an enclosed gas flow path extending between the pressurized pumping cell and a dispensing outlet port, the gas flow path having at least a first, second, and third spaced apart individually operable valve positioned in fluid communication therewith and located along the gas flow path, the first valve located upstream of the second valve closer to the optical pumping cell, wherein the gas flow path located intermediate the first, second, and third spaced apart valves define a first meted holding space with an associated volume that can be selectively closed off from the remainder of the gas flow path, the gas flow path, the dispensing port being located downstream of the first meted space; (c) a pressure sensor operably associated with the gas flow path; and (d) a control module operably associated with the first, second, and third spaced apart valves and the pressure sensor, the control module being configured to automatically direct the operational sequence of the opening and closing of the first, second, and third valves, wherein, in operation, the control module directs a plurality of hyperpolarized gas capture and release cycles, with the third valve closed, the control module sequentially closes the second valve, opens the first valve, and then closes the first valve to close the meted space from the remainder of the gas flow path to capture a discrete amount of hyperpolarized gas in the first meted space, and then the control module subsequently opens the second valve while the first valve is closed to release the discrete amount of hyperpolarized gas captured in the first meted space so that the discrete amount of hyperpolarized gas travels to the dispensing port.

In certain embodiments, the pressure reading is obtained once, at the start of the dispensing cycle.

Still other embodiments are directed to systems for dispensing hyperpolarized gas. The systems include: (a) means for evacuating and purging a gas flow path of contaminants; (b) means for dynamically adjusting in situ the aliquot amounts of a buffer gas and hyperpolarized gas desired to yield a patient bolus amount of a pharmaceutical product formulation; (c) means for automatically serially rapidly temporarily capturing and releasing discrete amounts of buffer gas to dispense a desired cumulative amount of buffer gas from the gas flow path into a gas dispensing outlet; (d) means for accumulating the captured and released discrete amounts of buffer gas exiting the dispensing outlet; (e) means for serially rapidly temporarily capturing and releasing discrete amounts of hyperpolarized gas to dispense a desired cumulative amount of hyperpolarized gas; and (f) means for accumulating the captured and released discrete amounts of hyperpolarized gas exiting the dispensing outlet.

Other embodiments are directed to methods of dispensing hyperpolarized gas formulations, including: (a) providing a pressurized hyperpolarized gas source; (b) directing the hyperpolarized gas from the hyperpolarized gas source to travel downstream from the hyperpolarized gas source in a predetermined enclosed gas flow path to an intermediate portion of the gas flow path; (c) capturing and releasing discrete amounts of the hyperpolarized gas by successively selectively temporarily closing off spaced apart portions of the intermediate portion of a gas flow path so that the intermediate portion of the gas flow path is isolated from the remainder of the gas flow path and then rapidly opening the closed intermediate portion of the gas flow path, the intermediate portion having a known volume; and (d) directing the discrete amounts of the captured and released hyperpolarized gas to travel downstream from the intermediate portion of the gas flow path to exit a gas dispensing port associated therewith to produce a first bolus of hyperpolarized gas product. The directing step may be carried out using existing system pressure.

Additional embodiments are directed to computer program products for operating a hyperpolarized gas dispensing system having a gas flow path with a plurality of spaced apart remote-controlled actuated valves that open and close to direct the flow of gas therein and to close off at least one intermediate portion of the gas flow path having a known volume. The computer program product includes: (a) a computer readable storage medium having computer readable program code embodied in said medium, said computer-readable program code comprising: (b) computer readable program code that obtains the pressure of a pressurized hyperpolarized gas source; (c) computer readable program code that obtains the polarization level of the hyperpolarized gas held in the hyperpolarized gas source; (d) computer readable program code the receives input about the desired formulation of hyperpolarized product, including at least one: the target bolus volume; the desired bolus polarization level percentage or concentration; the type of gas(es) to be dispensed to form the bolus; and the size and/or type of the bolus container; (e) computer readable program code that calculates the aliquot amount of hyperpolarized gas needed to produce the desired bolus formulation; (f) computer readable program code that calculates the number of capture and release actuations of predetermined ones of the actuated valves needed to dispense the calculated amount; and (g) computer readable program code that automatically transmits control signals to the predetermined ones of the remote actuated valves during operation of the dispensing system to cause selected valves to open and/or close at appropriate times so as to selectively temporarily close off a predetermined intermediate portion of the gas flow path having a known volume from the remainder of the gas flow path to capture a discrete amount of gas therein and to then rapidly open to release the captured discrete amount of gas therefrom.

In certain embodiments, the computer readable program code dynamically considers at a predetermined time in the dispensing protocol, and adjusts as needed, the aliquot amount of hyperpolarized gas needed to produce the desired bolus formulation for each successive dispensed bolus and re-calculates the number of capture and release actuations of predetermined ones of the actuated valves needed to dispense the calculated aliquot amount of hyperpolarized gas bolus to bolus.

Still other embodiments are directed to alternative computer program products for operating a hyperpolarized gas dispensing system having a gas flow path with a plurality of spaced apart remote-controlled actuated valves that open and close to direct the flow of gas therein and to close off at least one intermediate portion of the gas flow path having a known volume, the computer program product comprising a computer readable storage medium having computer readable program code embodied in said medium, said computer-readable program code comprising: (a) a capture and release cycle calculation module that calculates the number of valve actuation cycles needed to output a desired aliquot amount of polarized gas.

Certain embodiments provide systems and devices that can handle or dispense polarized gas in an automated or semi-automated manner by measuring, calculating, and adjusting quantities or parameters dynamically at the time of dispensing to produce patient-sized pharmaceutical grade quantities (such as, but not limited to, 0.5-2 liters) of polarized gas in a manner that can reduce the labor and/or variability involved therewith to produce the desired formulations to support to the clinic or hospital.

The foregoing and other objects and aspects of the present invention are explained in detail herein.

DETAILED DESCRIPTION OF EMBODIMENTS OF THE INVENTION

Figure 1:
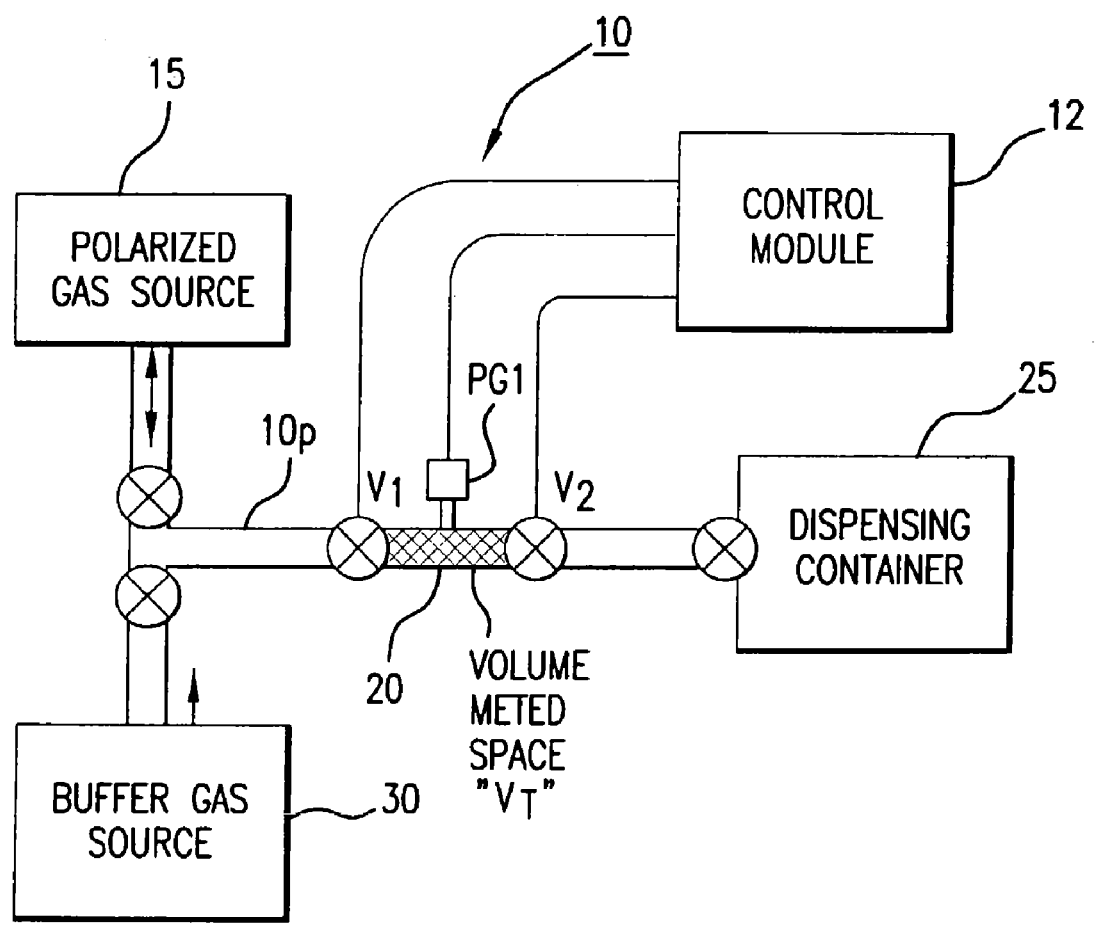
FIG. 1 is a schematic diagram of a pressurized meted dispensing system according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the drawings, layers, regions, or components may be exaggerated for clarity. In the figures, broken lines indicate optional features unless stated otherwise.

In the description of the present invention that follows, certain terms may be employed to refer to the positional relationship of certain structures relative to other structures. As used herein, the term "forward" and derivatives thereof refer to the general direction that a gas or gas mixture travels as it moves through the dispensing flow path; this term is meant to be synonymous with the term "downstream," which is often used in manufacturing environments to indicate that certain material being acted upon is farther along in the manufacturing process than other material. Conversely, the terms "rearward", "upstream" and derivatives thereof refer to the directions opposite, respectively, the forward and downstream directions.

Also, as described herein, polarized gases are collected and may, in particular embodiments, be frozen, thawed, and then used in MRI or NMR spectroscopy applications. For ease of description, the term "frozen polarized gas" means that the polarized gas has been frozen into a solid state. The term "liquid polarized gas" means that the polarized gas has been or is being liquefied into a liquid state. Thus, although each term includes the word "gas," this word is used to name and descriptively track the gas that is produced via a hyperpolarizer to obtain a polarized "gas" product. Accordingly, as used herein, the term "gas" has been used in certain instances to indicate a hyperpolarized noble gas product and may be used with modifiers such as solid, frozen, and liquid to describe the state or phase of that product. The polarized gas product may include other constituents such as other carrier or buffer gases or carrier liquids as desired.

Various techniques have been employed to accumulate and capture polarized gases. For example, U.S. Pat. No. 5,642,625 to Cates et al. describes a high volume hyperpolarizer for spin-exchange polarized noble gas and U.S. Pat. No. 5,809,801 to Cates et al. describes a cryogenic accumulator for spin-polarized $^{129}$Xe. As used herein, the terms "hyperpolarize," "polarize," and the like, are used interchangeably and mean to artificially enhance the polarization of certain noble gas nuclei over the natural or equilibrium levels. Such an increase is desirable because it allows stronger imaging signals corresponding to better MRI images or spectroscopic NMR signals of the substance in a targeted area of the body or in other in vitro or ex vivo targets of interest.

As is known by those of skill in the art, hyperpolarization can be induced by spin-exchange with an optically pumped alkali-metal vapor or alternatively by metastability exchange. See Albert et al., U.S. Pat. No. 5,545,396. Other polarization techniques may also be employed, such as, but not limited to, thermal polarization, dynamic nuclear polarization (DNP), and/or para-hydrogen induced polarization.

In particular embodiments, the "target" gas or gas to be polarized may be a noble gas, such as $^{129}$Xe or $^{3}$He. Other target gases may also be used, alone or in combinations. The target gas may be polarized, for example, by optically pumped spin-exchange with a vapor comprising an alkali metal, such as $^{85}$Rb and/or $^{87}$Rb. Other alkali metals may also be used, alone, or in combinations. Exemplary lists of alkali metals are provided in the above-incorporated U.S. Pat. No. 5,545,396 and U.S. Pat. No. 6,318,092, the disclosures of which are hereby incorporated herein by reference as if set forth fully herein in their entireties. In other embodiments, the target gas may comprise $^{13}$C, $^{19}$F, and/or $^{15}$N, or other isotope of interest, such as small organic molecules enriched in $^{13}$C. In particular embodiments, these target gases which may be polarized using dynamic nuclear polarization (DNP) and/or para-hydrogen induced polarization.

The polarized gas may be combined with a buffer gas or filler gases such as non-polarized inert noble gases that are polarization friendly, such as, but not limited to, one or more of medical grade nitrogen, helium, argon, and the like. Examples of filler or buffer gas formulations are described in the above-incorporated U.S. Pat. No. 6,295,834.

The present invention is described in certain portions of the specification with reference to flowchart illustrations and/or block diagrams of methods, and computer program products according to certain embodiments of the invention. It will be understood that each block of, the flowchart illustrations and/or block diagrams, and combinations of blocks in the flowchart illustrations and/or block diagrams, can be implemented by computer program instructions. These computer program instructions may be provided to a controller or processor of a general purpose computer, special purpose computer, embedded processor or other programmable data processing apparatus to produce a machine, such that the instructions, which execute via the processor of the controller or computer or other programmable data processing apparatus, create means for implementing the functions specified in the flowchart and/or block diagram block or blocks.

These computer program instructions may also be stored in a computer-readable memory that can direct a controller or computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a controller or computer or other programmable data processing apparatus to cause a series of operational steps to be performed on the controller or computer or other programmable apparatus to produce a computer implemented process such that the instructions which execute on the computer or other programmable apparatus provide steps for implementing the functions specified in the flowchart and/or block diagram block or blocks.

As will be appreciated by one of skill in the art, the present invention may be embodied as a system, method, data or signal processing system, or computer program product, and may include certain electromechanical or hardware components. Accordingly, certain embodiments of the present invention may take the form of an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as LABVIEW, Java7, Smalltalk or C++. However, the computer program code for carrying out operations of the present invention may also be written in conventional procedural programming languages, such as the "C" programming language or even assembly language. The program code may execute entirely on the user's controller or computer, partly on the user's controller or computer, as a stand-alone software package, partly on the user's controller or computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain of the flowcharts and block diagrams illustrate methods to operate dispensing systems or components thereof to yield desired sequential discrete aliquots of adjustable bolus allocations of polarized gas product formulations according to embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 5:
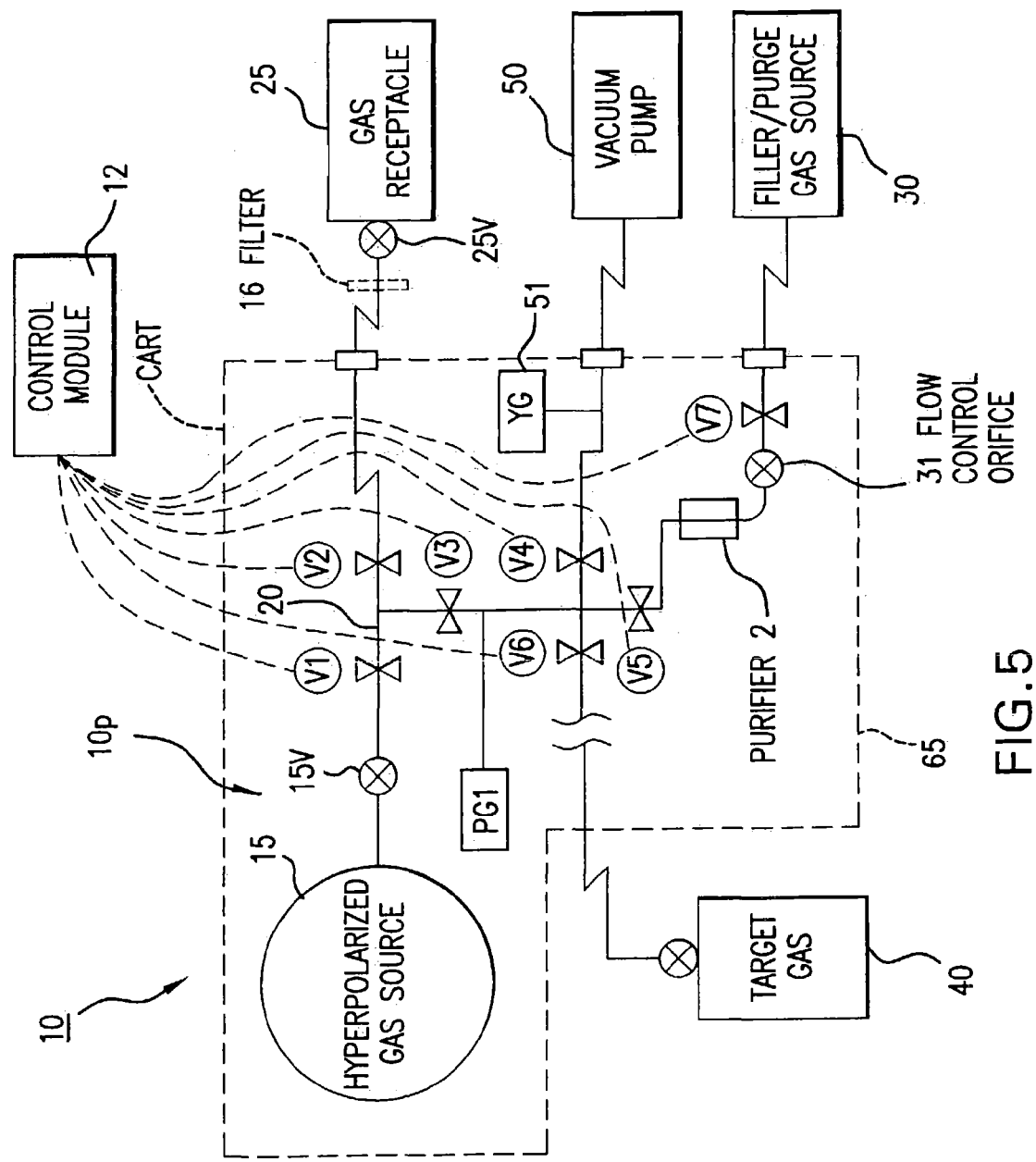
FIG. 5 is a schematic illustration of a hyperpolarized gas dispensing system according to embodiments of the present invention.

Turning now to FIG. 1, a gas dispensing system 10 is illustrated. The gas dispensing system 10 may be configured to direct the flow of one or a plurality of different source gases or gas mixtures in the system itself and/or to the receiving container 25. As shown, the gas dispensing system 10 includes an enclosed gas flow path 10$p$ that extends between a hyperpolarized gas source 15 and a dispensing container or receptacle 25. The gas dispensing system 10 also includes a controller 12 operably associated with at least two spaced apart valves $V_1$, $V_2$, that define at least one meted holding space 20 with an associated predetermined volume $V_T$ (illustrated by the cross-hatched markings in an intermediate portion of the gas flow path 10$p$ between the opposing valves $V_1$, $V_2$) that can be selectively sealed from the remainder of the gas flow path 10p. The system 10 can also be configured to dispense a buffer or filler gas. As shown, in certain embodiments, the gas flow path 10p can be adapted to allow a pressurized buffer or filler gas source 30 to be attached thereto. The dispensing system 10 can also include at least one pressure sensor, such as a pressure gage or transducer, shown as PG1, positioned in at least one desired location along the gas flow path 10p. In the embodiment shown, the pressure sensor PG1 is positioned in the meted space 20. Other locations may also be used that are able to provide sufficiently reliable pressure information about the pressure in the appropriate portion of the gas flow path 10p. In certain particular embodiments, the pressure sensor PG1 is positioned upstream of the meted space 20. FIG. 5 illustrates one such upstream embodiment. Positioning the pressure sensor PG1 in a position that reduces the amount of contact time with hyperpolarized gas during dispensing can reduce the loss in polarization associated therewith.

In operation, the control module 12 is operably associated with the valves $V_1$, $V_2$, and the pressure sensor PG1. The control module 12 is configured to direct the operational sequence of the opening and closing of the valves $V_1$, $V_2$. Thus, in operation, the control module 12 directs a plurality of capture and release cycles, with each cycle being carried out so that the control module 12 sequentially closes the downstream valve $V_2$, opens the upstream valve $V_1$, then closes the upstream valve $V_1$ to close the meted space 20 to capture a discrete amount of gas in the meted space 20. The control module 20 subsequently opens the downstream valve $V_2$ while the upstream valve $V_1$ is closed to release the discrete amount of gas captured in the meted space 20 so that the discrete amount of gas travels in a predetermined direction downstream of the meted space 20. In certain embodiments, the plurality of capture and release cycles can be carried out for at least one aliquot quantity of gas, and typically two aliquot quantities of different gas or gas mixtures, in less than about 5 minutes to dispense a plurality of discrete amounts of gas sufficient to yield the desired cumulative amount of gas into the dispensing container 20. For dispensing polarized gas mixtures, the successive repetition of the sequence of operations may be carried out rapidly to reduce the time the gas is held in the meted space and inhibit polarization degradation.

At the time of initialization for a particular quantity of polarized gas product, the system 10 can receive as input the known pressure of the gas flow path proximate the meted space 20 and the predetermined volume $V_T$ of the meted space 20 is already known. As such, the system 10 can calculate the number N of capture and release cycles needed to emit the serially dispensed discrete quantities of gas according to the universal gas law (PV=nRT). The number of capture and release cycles N can be determined proximate in time to, or at the onset of, the actual dispensing of the gas or gas mixture, or can be determined during the dispensing procedure. In certain embodiments, the number of capture and release cycles N can be automatically determined once at the beginning of the dispense sequence for each bolus or aliquot of hyperpolarized gas (and again for any additional aliquot of another gas or gas mixture) dispensed into the container 25.

The mathematical relationship expressed by Equation (1) below may be used to calculate the number N of capture and release cycles suitable for dispensing the desired aliquot of hyperpolarized gas. Similar equations can be used to determine the number N of capture and release cycles for dispensing filler or buffer gas. In the latter situation, the buffer/filler gas source may be provided at a substantially constant pressure as will be discussed further below.

In any event, the number N of capture and release cycles can vary depending on one or more of the end volume desired, whether filler or buffer gas is desired to form a blended gas product suitable for in vivo administration or other desired use, the receiving container size and/or shape, the polarization percentage blend or concentration desired, the polarization level of the gas at the time of dispensing, and the desired end use application of the gas product. Thus, in certain embodiments, the system can dynamically adjust, in situ, the number N used to provide the desired formulation. The pressure reading and/or polarization level may decrease after the first dispensing cycle and the system 10 can be configured to automatically adjust for these decreases. For example, the system 10 can either mathematically estimate the pressure decrease or take measurements thereof.

In particular embodiments, the number N of cycles used to dispense the discrete meted quantities can be determined using the universal gas law and known or measured pressures and volumes. The following equations or similar mathematical expressions can be used where appropriate to determine the number of cycles N for a desired dispensed volume. In these equations, "K" is a constant, "N" is the number of capture and release cycles, "$P_N$" is the pressure at capture release cycle "N", "$V_C$" is the volume of the container of the polarization source (which can be an optical pumping cell, as will be discussed further below), $V_T$ is the volume of the meted space, $P_0$ is the original pressure (at ambient temperature for the model shown), $P_{atm}$ is atmospheric pressure (the pressure of the dispensing container), and $V_{disp}$ is the dispensed volume. The constant "K" will vary according to the volume of the meted space. Thus, if two different meted spaces are used, two different "K" constants can be used to determine the number of meted aliquots associated with each meted spaced used.

$$K = V_C / (V_C + V_T) \qquad \text{Equation (1)}$$

To determine the number of cycles needed to dispense a desired cumulative dispensed quantity or the aliquot hyperpolarized gas quantity, the integrated individual dispensed values can be summed as follows. $P_0$ represents an initial pressure, the "G" next to the pressure reading indicates that it is a "gauge" pressure. $V_{disp}(N)$ is the amount of gas captured for a respective capture and release cycle (the amount in the meted space can vary as the upstream pressure declines over the dispensing cycles) and $V_{disp}$ is the cumulative dispensed amount for N capture and release cycles. The relationship of pressures in the gas flow path 10p including $P_0$ (the pressure of the pressurized gas source just prior to the first capture and release cycle), $P_N$ (the pressure at a respective capture and release cycle) and $P_{atm}$ (atmospheric pressure, the pressure of the receiving container) can be expressed by the following equations.

$$P_{N,G} = P_{O,G} K^N \qquad \text{Equation (2)}$$

$$V_{disp(N)} = \frac{(P_{O,G} - P_{N,G})V_C}{P_{atm}} = [P_{O,G} - P_{O,G}(K)^N]\frac{V_C}{P_{atm}} \qquad \text{Equation (3)}$$

$$V_{disp(N)} = \frac{P_{O,G}}{P_{atm}}(1 - (K)^N)V_C \qquad \text{Equation (4)}$$

Equation (4) can be solved for N to determine the number of dispense cycles to yield a desired dispensed volume $V_{disp}$ $$\frac{V_{disp}}{V_C} \times \frac{P_{atm}}{P_{O,G}} = 1 - K^N \quad \text{Equation (5)}$$

$$K^N = 1 - \frac{V_{disp}}{V_C} \times \frac{P_{atm}}{P_{O,G}} \quad \text{Equation (6)}$$

$$N = \frac{\ln\left(1 - \frac{V_{disp}}{V_C} \frac{P_{atm}}{P_{O,G}}\right)}{\ln K} \quad \text{Equation (7)}$$

For embodiments using constant pressure, the number of cycles can be calculated more directly based on the universal gas law noted above, with the pressure in the meted space being assumed to be substantially constant and equivalent to the pressure in a pressurized cylinder and/or at least a regulated space, i.e., at a regulator. Thus, the pressure in the upstream line (and assuming the temperature is substantially constant) can be assumed to be substantially constant over each capture and release cycle, making the computation relatively non-complex.

In any event, in operation, the dose concentration and/or polarization gas volume desired for a particular dispensed aliquot of a desired gas using the gas flow system 10 (such as hyperpolarized gas, target gas, and/or buffer or filler gas) can be dynamically determined and output in situ using a control module 12 with computer program code and communication means that allows receive and transmit signals to be relayed to the valves in the gas flow path 10p. As used herein, the term "dynamically" means that the pressure is automatically measured at least once proximate in time to the actual dispensing procedure and/or that the desired number of dispensable meted quantities are determined automatically in situ proximate in time to the time of dispensing one or each aliquot of gas.

The control module 12 can include a controller or signal processor that can be configured to receive and process a pressure measurement associated with the meted space or other relevant (upstream) portion of the gas flow path 10p and/or to semi-automatically or automatically direct the sequence of operation of the valves during dispensing.

The pressure in the dispensing system 10 can be within any suitable range that provides sufficient pressure to allow the desired gas to flow downstream to the dispensing container 25 from the source container(s) 15 (and 30, where used, and also 40 in FIG. 5) and that allow for the operational range of the remote or automatically activated valves. In certain embodiments, the system 10 can operate in the 15-180 psig range, with typical operation above about 60 psi. In certain embodiments, when directing the flow of buffer/filler or target gas, the pressure in the relevant portions of the gas flow path 10p can be about 80-130 psi, and in particular embodiments about 80-82 psi (for buffer/filler gas) and about 110-130 psi (for target gas). The hyperpolarized gas source 15 may be configured to operate with at least an initial dispensing pressure of about 2-10 atm.

The valves $V_1$, $V_2$ may be electrically, pneumatically, and/or hydraulically controlled. In certain embodiments, the valves $V_1$, $V_2$ are digitally controlled for rapid response. As used herein, the term "rapid" means that one capture and release cycle can be carried out in less than about 5 seconds, and typically in less than about 1s, or so that the capture and release cycles can be carried out so that one bolus or aliquot of hyperpolarized gas (such as 0.25-1.5 liters) can be dispensed in a plurality of discrete meted quantities in less than about 60 seconds, and typically less than about 20-30 seconds. Suitable valves are available from FABCO-Air, Inc. of Gainesville, Inc.

Figure 2A:
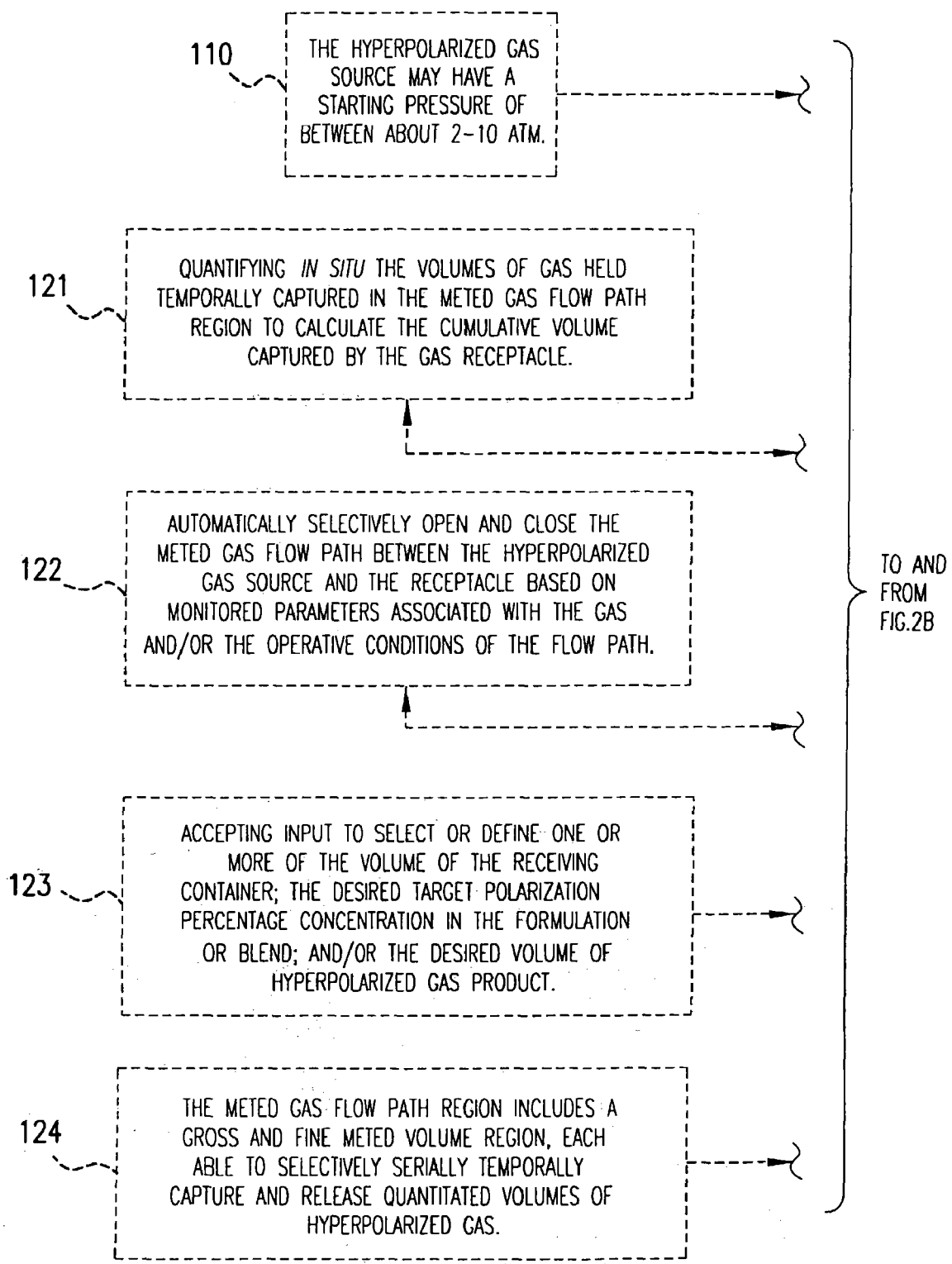
FIG. 2 is a block diagram of operations used to dispense hyperpolarized gas according to embodiments of the present invention.
Figure 2B:
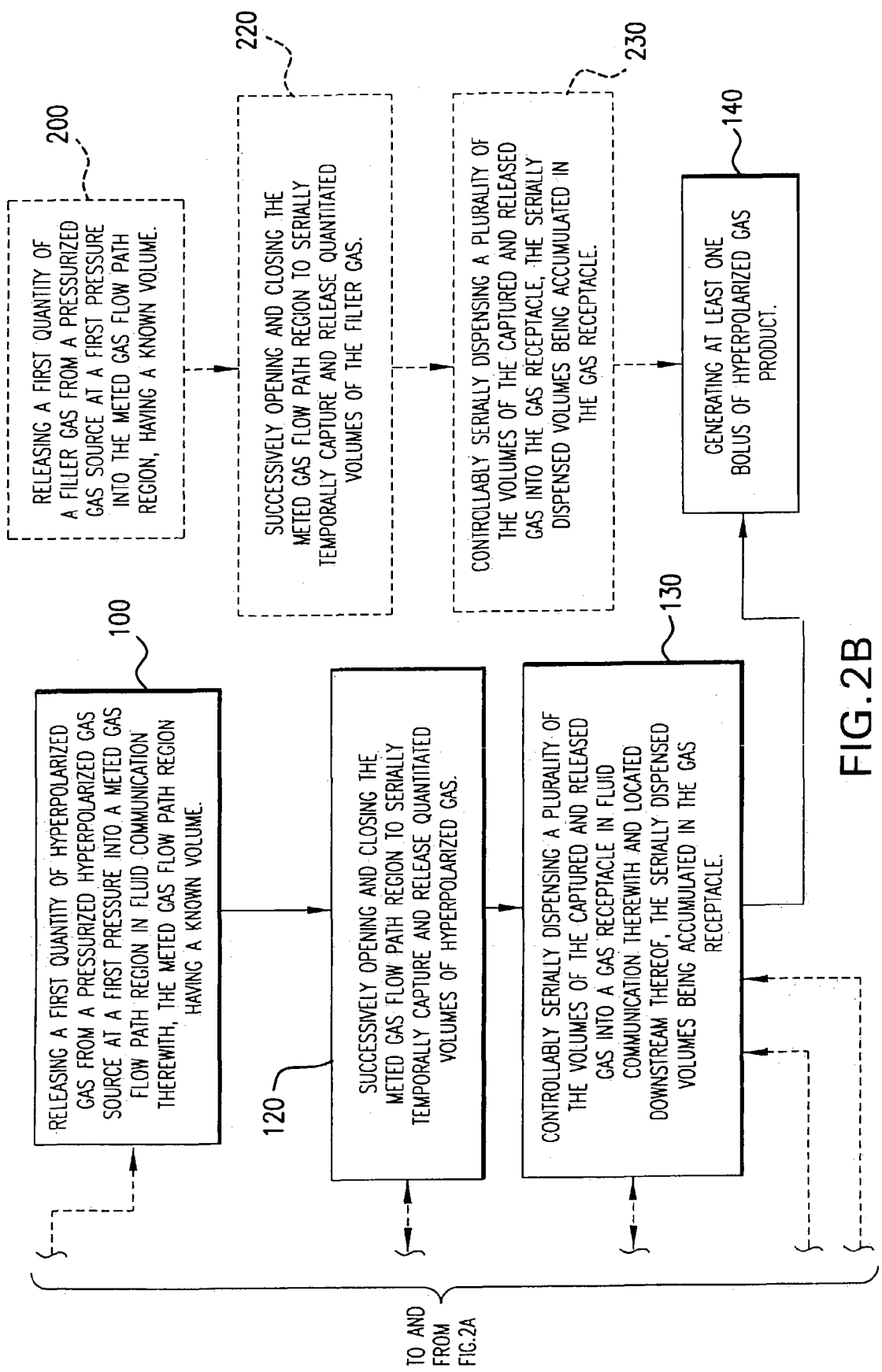

FIG. 2 illustrates exemplary operations for the dispensing system 10. A first quantity of hyperpolarized gas is released from a pressurized hyperpolarized gas source at a first pressure into a meted gas flow path region in fluid communication with the source. The meted gas flow path region has a second lower pressure and a known volume (block 100). The meted gas flow path region can be successively opened and closed to serially capture and release discrete quantitated amounts of hyperpolarized gas (block 120). A plurality of the discrete captured and released volumes can be serially controllably dispensed into a gas receptacle in fluid communication with the meted gas flow path and located downstream thereof so that the serially and controllably dispensed gas is accumulated in the gas receptacle (block 130). This accumulated gas can be used to define one bolus or aliquot of hyperpolarized gas.

In certain embodiments, the hyperpolarized gas source can have a starting pressure of between about 2-10 atm (block 110). The container itself may be configured with a known initial pressure and volume. The initial pressure gradually decreases during dispensing (container-to-container or even between successive discrete meted portions). The volumes of gas held temporarily captured in the meted gas flow path region can be quantified in situ to calcuate the cumulative volume released to and captured by the gas receptacle (block 121). The meted gas flow path can be automatically selectively opened and closed between the gas source and the gas receptacle based on monitored parameters associated with the gas and/or the operative conditions of the gas flow path (block 122). User input can be accepted to define one or more of: (a) the volume or type of the receiving container; (b) the desired bolus formulation; (c) the desired target polarization percentage or concentration in the formulation; and (d) the desired gas constituents or total combined cumulative volume of a blended formulation (block 123). The polarization level of the polarized gas to be dispensed may be input by the user or automatically relayed from a polarimetry system proximate in time to initiation of the dispensing protocol.

In certain embodiments, the meted gas flow path region includes a gross or coarse volume region and a fine volume region (see, e.g., FIGS. 6A, 6B), each being selectively activatable to serially capture and release desired numbers of discrete amounts of gas (block 124). That is, at least three different spaced apart valves, $V_1$, $V_2$, $V_3$ (located downstream of $V_2$), can be used to selectively define the meted space used to capture and release discrete quantities of gas. In this embodiment, the intermediate valve $V_2$ can remain open during the capture and release cycle that uses the meted volume closed off from the remainder of the gas flow path by $V_1$ and $V_3$.

In certain embodiments, similar to the operations used to dispense hyperpolarized gas, the operations can be carried out to dispense a (non-polarized) filler/buffer gas. That is, a first quantity of a filler gas can be released from a pressurized gas source to the meted gas flow path region (block 200). The meted gas flow path region can be successively opened and closed off from the remainder of the gas flow path to serially capture and release successive quantities of discrete meted volumes of filler gas (block 220). The successive quantities of discrete captured and released gas can be controllably and serially dispensed into the gas receptacle and accumulated therein (block 230). The aliquot of filler gas can be directed into the gas receptacle prior to dispensing the hyperpolarized gas therein, to reduce the dwell time of the hyperpolarized gas in the container and/or exposure to processing conditions during dispensing of the filler gas and inhibit depolarization associated therewith. The aliquot of filler/buffer gas can be combined with the aliquot of hyperpolarized gas to generate the desired blends to produce the bolus of hyperpolarized gas product (block 140). The aliquot and/or the number of capture and release cycles can be determined automatically in situ (using program code and measured or monitored parameters and/or user input), based on one or more of the polarization level of the polarized gas, the desired percentage of polarization, the desired cumulative total, and the like.

Figure 3:
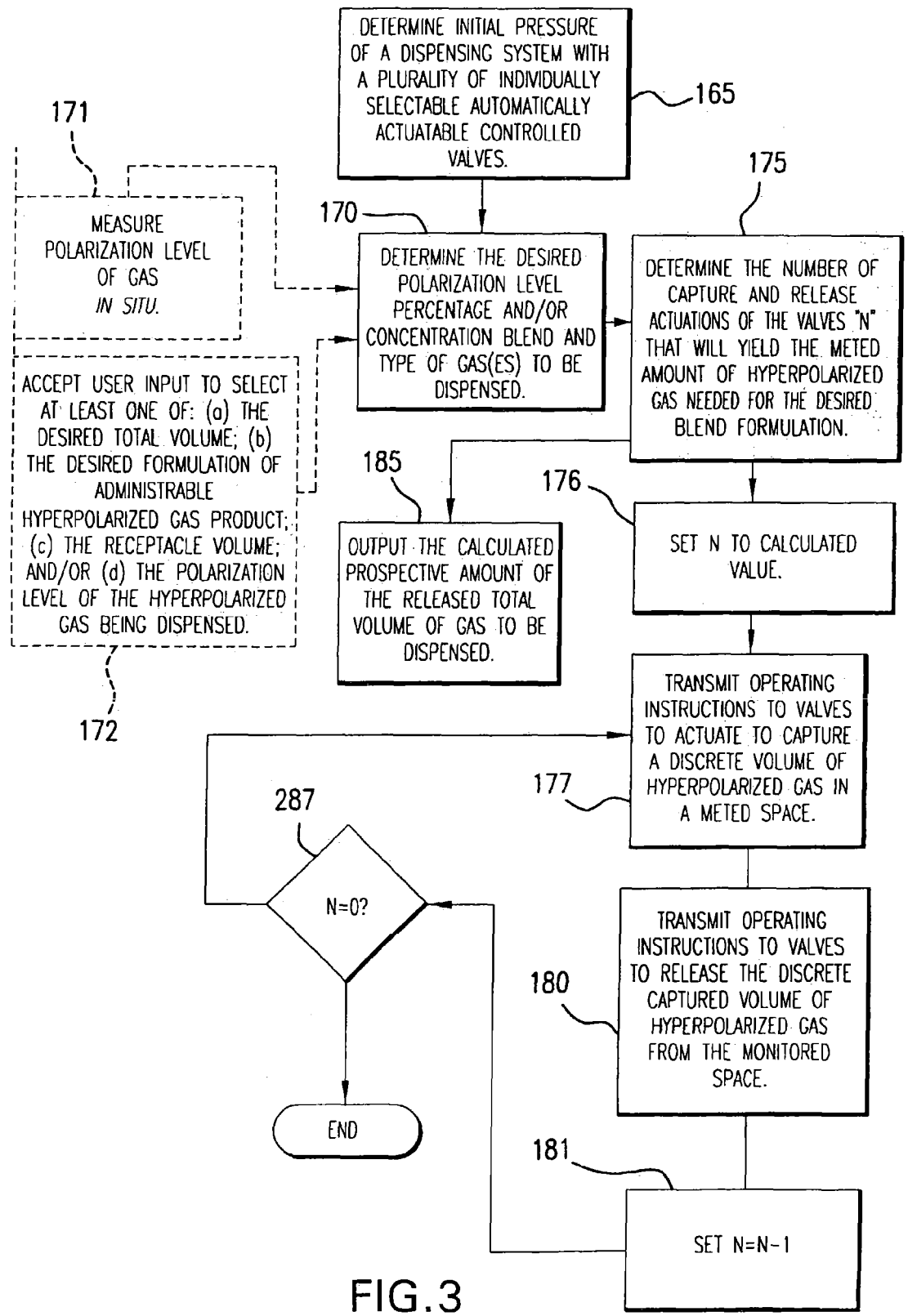
FIG. 3 is a flow diagram of operations that can be used to dispense hyperpolarized gas products according to embodiments of the present invention.

FIG. 3 illustrates operations that may be carried out according to certain embodiments of the present invention. As shown, the initial pressure of a dispensing system having a plurality of individually selectable automatically controlled valves can be determined (block 165). The desired polarization level percentage and/or concentration blend and/or type of gases to be dispensed to provide the desired hyperpolarized product can be determined or identified (block 170). In certain embodiments, the polarization level of the polarized gas to be dispensed may be measured in situ proximate in time to initiation of the dispensing procedure (block 171). The system may be configured to accept user input (touch screen, keyboard, voice recognition, and the like) to select at least one of: (a) the desired total bolus volume; (b) the formulation of the administrable hyperpolarized gas product; (c) the receptacle volume and/or type; and (d) the polarization level of the gas (block 172). These items may be programmed to be identified by clinician selection of the end use, i.e., container type such as I, II, III (which can be preprogrammed with known relevant parameters such as size, shape, desired fill volume, etc), inhalation image for lungs (having a default value of about 0.5-1.5 L cumulative bolus), and % polarization (which can have a default set at a minimum desired strength for the bolus for the particular application). In certain embodiments, the operations can be programmed and configured to dynamically calculate the quantities of filler gas and/or hyperpolarized gas based on user or measured input, default values, or other established data. These aliquots can be adjusted dynamically and can vary, container to container.

The number of capture and release actuations of the valves "N" needed to yield the meted amount of hyperpolarized gas (and/or buffer or filler gas) for the desired formulation can be calculated or determined. The number "N" can be set to the determined number at the initiation of the dispensing protocol. Where both buffer/filler gas and hyperpolarized gas will be dispensed (serially), the number N can be determined separately for each type gas. Further, when more than one meted space volume ($V_T$) can be selected, the operations can be carried out to select the number N for each combination of the different volumes that will yield the quantity closest to that desired. The calculated prospective amount of released volume of gas to be dispensed can be output (block 185). That is, it is possible that the desired formulation quantity and the actual dispensed quantity may vary as the discrete amounts may not cumulatively provide the exact desired quantity, but may exceed or fall short of the desired number in order. Operating instructions are transmitted to the valves to actuate to capture a discrete volume of (hyperpolarized) gas in a meted space (block 177). Operating instructions are then transmitted to the valves to release the discrete capture volume of (hyperpolarized) gas (block 180). The number of actuation cycles N is then decremented by one. If the number of cycles is equal to zero, the operation can be terminated or restarted to dispense another aliquot of gas. If the number N is greater than one, then the operations described in blocks 177 and 180 are repeated. As noted above, if non-polarized gas is dispensed these operations can be performed for that gas in advance of dispensing the hyperpolarized gas.

Figure 4:
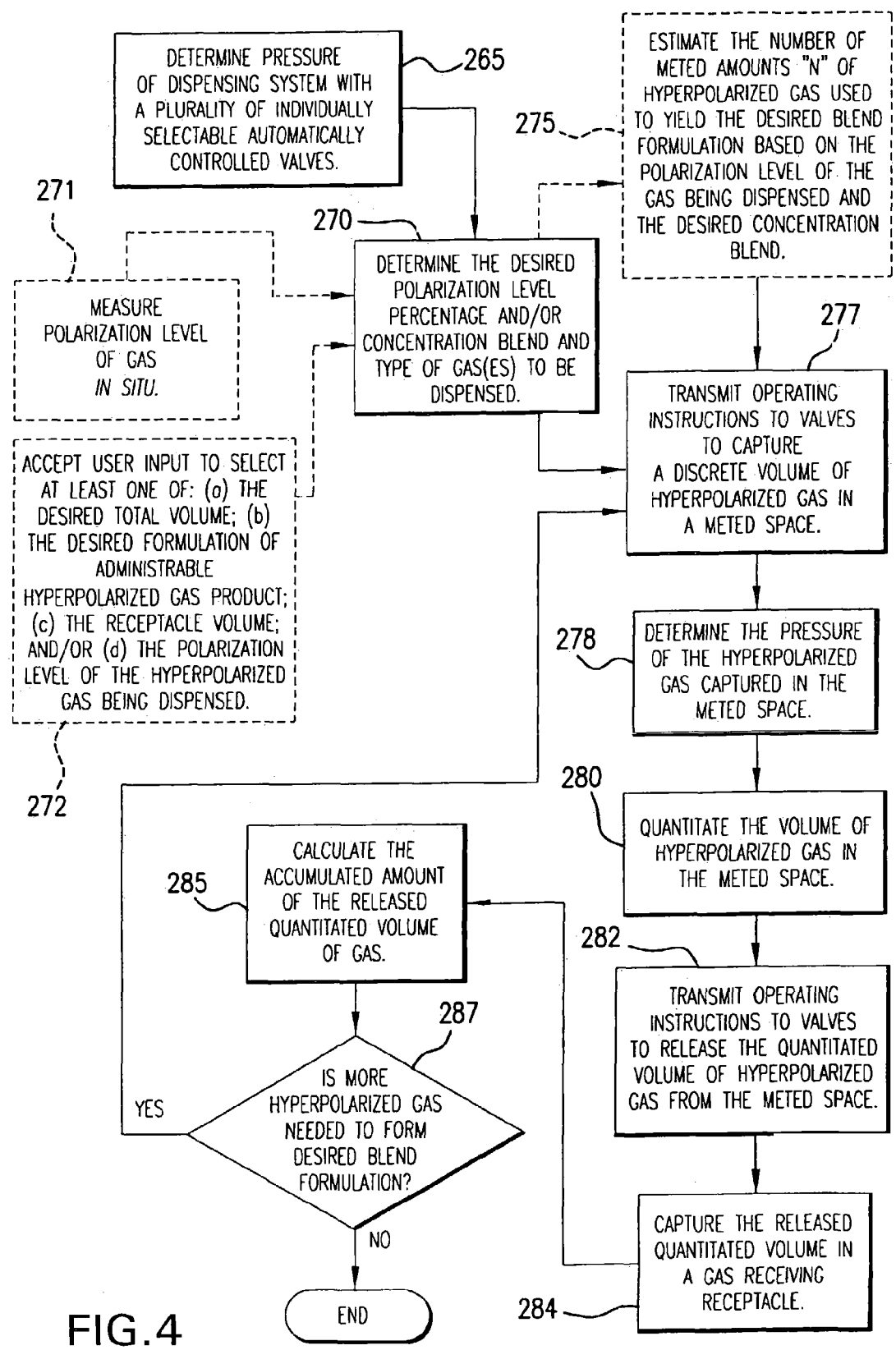
FIG. 4 is a flow diagram of operations that can be used to dispense hyperpolarized gas products according to additional embodiments of the present invention.

FIG. 4 illustrates another series of operations that can be carried out to dispense gas according to embodiments of the present invention. In this embodiment, a plurality of pressure measurements can be carried out in situ during the dispensing protocol of each aliquot of gas to determine if additional quantities of gas should be released. As before, a pressure of the dispensing system can be established (block 265). The polarization level percentage and/or concentration blend and type of gases desired for the end product formulation can be determined (block 270). Similar to operations described with respect to FIG. 2 and/or 3, the polarization level may be measured (block 271) and user input can input relevant data (block 272). If desired, the number of meted amounts of hyperpolarized gas used to yield the desired blend formulation based on the polarization level of the gas being dispensed and the desired blend concentration/polarization percentage may be optionally estimated (block 275). Operating instructions are transmitted to the valves to cause them to capture a discrete volume of hyperpolarized gas in the meted space (block 277). The pressure associated with the meted space can be determined (block 278) and the volume of gas in the meted space can be calculated (block 280). Operating instructions can be transmitted to cause the valves to release the discrete meted volume from the meted space (block 282). The released gas can be captured in the receiving receptacle or container (block 284). The accumulated amount can be calculated (block 285) and it can be determined whether additional gas is needed to form the desired blend formulation (recognizing the next released amount will be within certain ranges that may put the desired target amount well above what is needed or make it below what is needed). Thus, acceptable dose ranges can be input into the operations to define suitable dose formulations. If so, the operations described in (blocks 277-287) can be repeated. If not, the operations can be terminated.

FIG. 5 illustrates one example of a dispensing system 10 according to certain embodiments of the present invention. As shown, the system 10 includes a plurality of spaced apart valves positioned along the gas flow path 10p. The valves $V_1$-$V_7$ may be individually automatically activated by the control module 12 to selectively direct the flow of a plurality of different gas and gas mixtures in the system 10. Additional or fewer gas sources may also be employed. As shown, the system 10 can include three different pressurized gas sources: a target gas source 40; a filler/purge gas source 30; and the hyperpolarized gas source 15. The system 10 may be housed in a cart 65 or other structure. The walls of the cart 65 are illustrated in broken line; those components to the outside of the broken line may be mounted to the cart 65 and are in communication with certain of the components to the inside of the broken line. The control module 12 may be also housed internally of the cart 65 or mounted so as to provide externally accessible user input peripheral equipment or displays. The cart 65 may be portable or configured to reside in a particular use location (which may be at the clinic site). The target gas source 40 and filler/purge gas sources 30 may be mounted as shown to allow for easier external access and field replacement of the container sources. As shown, a pressure gage (PG1) may be positioned below valve $V_3$ outside a meted region 20 that is defined by the region between $V_1$, $V_2$ and $V_3$.

In this embodiment, the hyperpolarized gas source 15 may be an optical pumping cell that is used to polarize the gas in situ while the optical pumping cell 15 is held on the cart 65. Additional description of the optical pumping cell will be provided below.

As is also shown in FIG. 5, the system 10 can include a vacuum pump 50, a vacuum gage 51, and one or more flow control orifices 31. The gas receptacle 25 can be a rigid container formed and/or coated of a material or materials that are polarization friendly (i.e., they do not unduly decay the polarization of the polarized gas), such as an aluminosilicate (e.g., PYREX material) container, a sol-gel coated container, or a resiliently configured collapsible container (such as an elastomeric bag). For additional description of suitable resilient containers and materials, see co-pending U.S. patent application Ser. No. 09/334,400, the contents of which are hereby incorporated by reference as if recited in full herein.

Figure 6A:
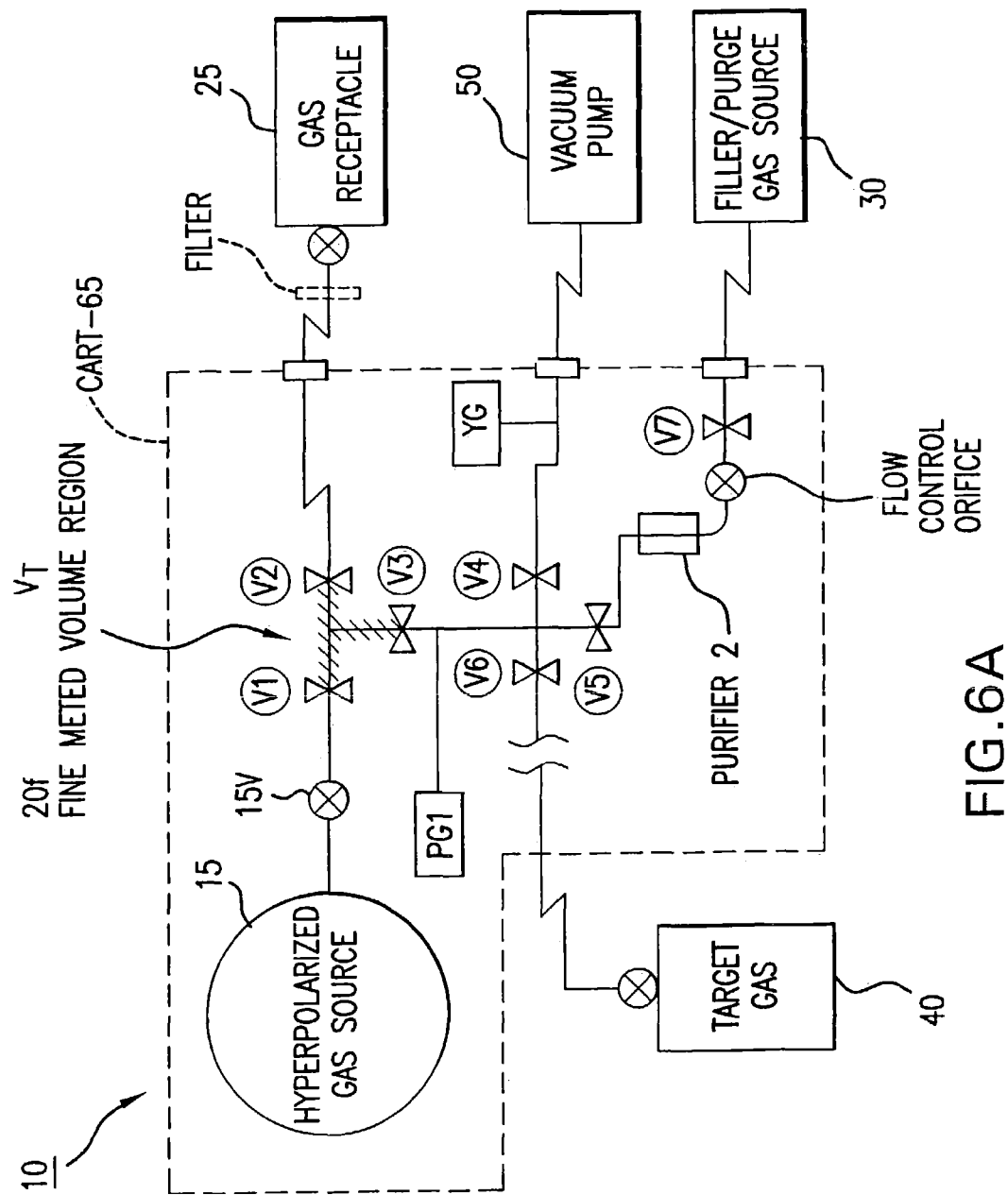
FIG. 6A illustrates a first meted volume region in the flow path of FIG. 5 in the system according to embodiments of the present invention.
Figure 6B:
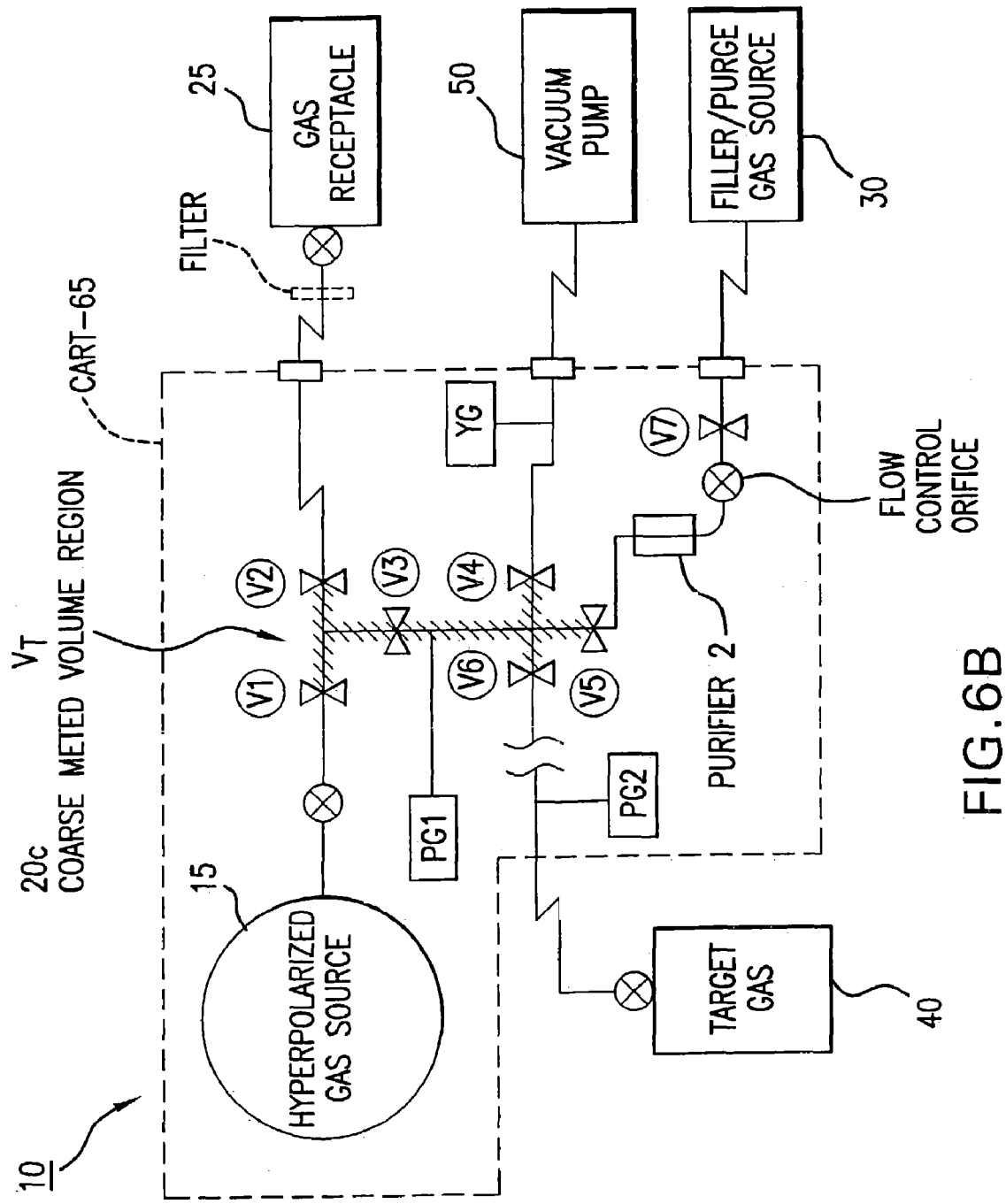
FIG. 6B illustrates a second meted volume region in the flow path of FIG. 5 in the system according to embodiments of the present invention.
Figure 10:
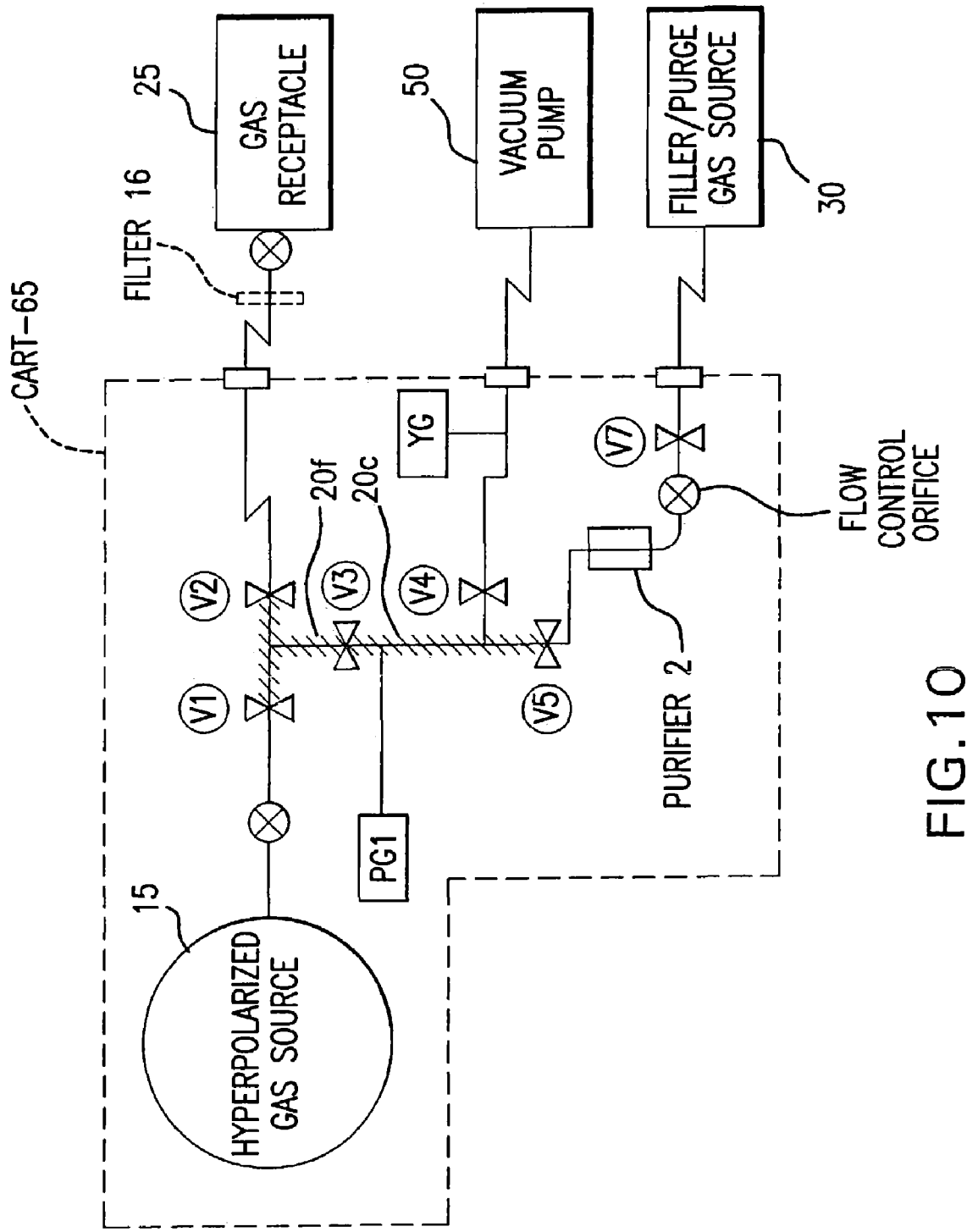
FIG. 10 is a schematic illustration of a hyperpolarized gas dispensing system according to embodiments of the present invention.

FIGS. 6A and 6B illustrate that the system 10 can include a plurality (shown as two) different independently selectable meted regions 20; a fine or smaller meted volume region 20f shown by the hatch lines in FIG. 6A; and a coarse or larger meted volume region 20c shown by the hatch lines in FIG. 6B. As shown, the meted volume $V_T$ defined by coarse region 20c includes the meted volume defined by the fine region 20f. That is, as shown in FIG. 6A, with the valves closed, the region or bounded by spaced apart valves $V_1$, $V_2$, and $V_3$ provides the fine meted volume 20f that can be isolated from the remainder of the flow path. In contrast, as shown in FIG. 6B, the region bounded by spaced apart valves $V_1$, $V_2$, $V_4$, $V_6$ and $V_5$ defines the coarse meted space 20c. In other embodiments, such as when the hyperpolarized gas source is engaged already polarized and the system does not require a target gas source, as shown in FIG. 10, the coarse volume 20c can be defined by the region bounded by valves $V_1$, $V_2$, $V_4$ and $V_5$.

In certain embodiments, the volume $V_T$ associated with fine meted space 20f may be sized in the range of about 1-20 cc's, typically about 3-5 cc's, while the larger or coarse meted space 20c may have a volume $V_T$ of about 50-150 cc's, typically about 100 cc's. These quantities can be adjusted as desired by configuring the internal volume of the flow relevant portion of the flow path 10p and/or the placement of the appropriate isolating valves to provide the desired volumes.

The system 10 can include one or more purifiers or filters (identified as "purifier" and "filter" as shown in FIG. 5) can be positioned in line with the plumbing to remove impurities such as water vapor, alkali metal (post polarization), and oxygen from the system (or to inhibit their entry therein). The placement of the rubidium filter 16 is shown outside the walls of the cart adjacent the container 25. This placement allows for easy field replacement. It is expected that the filter 16 can be replaced at desired intervals, such as about every 50-52 dispensings.

The system 10 can also include various sensors including a flow meter as well as a plurality of valves as well as electrical solenoids, and/or hydraulic or pneumatic actuators that can be controlled by the control module 12 to define the flow path 10p and operation of the components of the system 10. As will be understood by those of skill in the art, other flow control mechanisms, and devices (analog and electronic) may be used as contemplated by the present invention.

Figure 7:
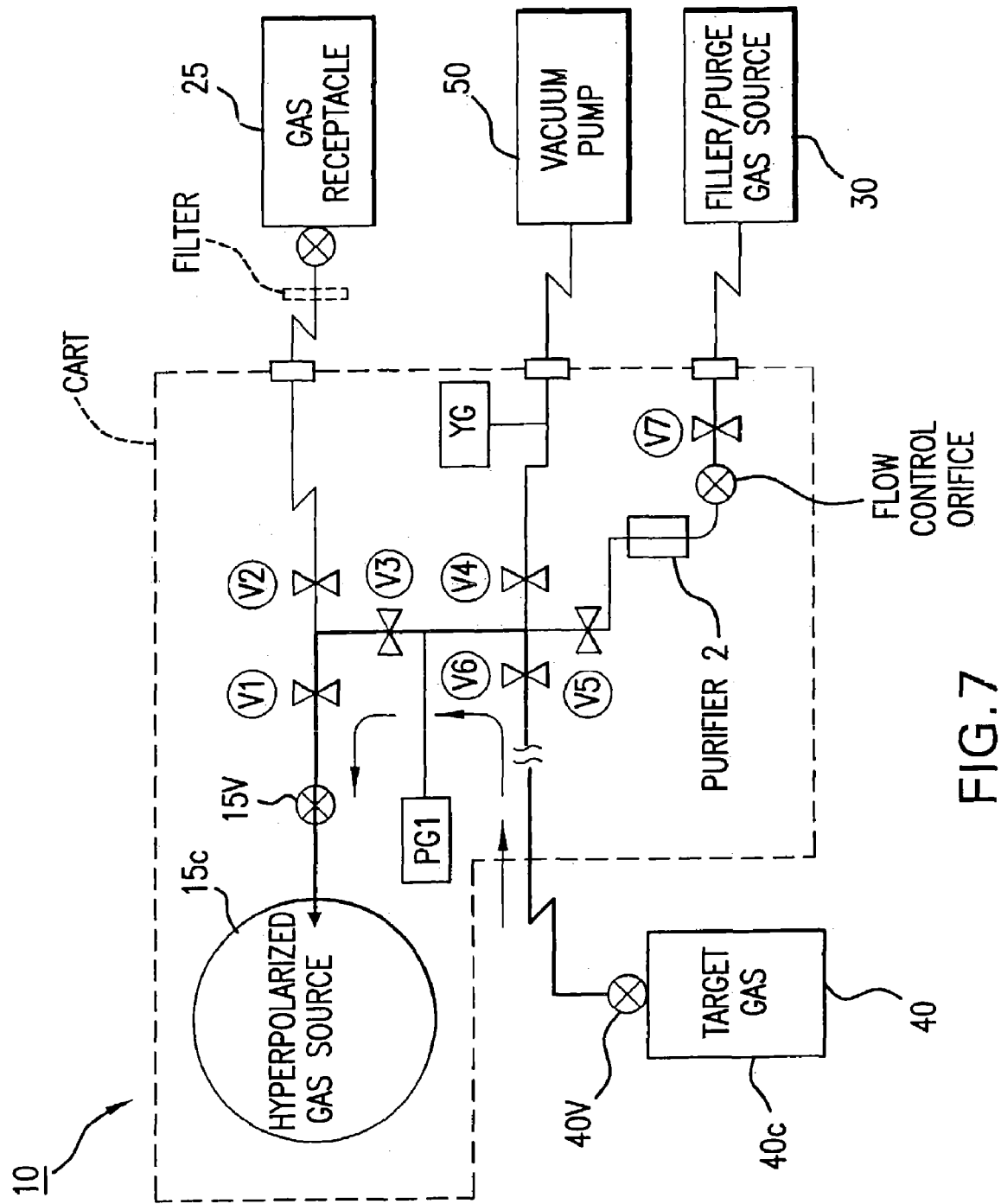
FIG. 7 illustrates a flow path of a target gas used to fill an optical pumping cell prior to polarization in the system of FIG. 5 according to embodiments of the present invention.

In operation, as shown in FIG. 7, the target gas 40 may be directed to flow into the optical pumping cell 15c. To do so, the valve 40v associated with the target gas container 40c itself is opened and, in the system 10, valves $V_2$, $V_4$, $V_5$ are closed and valves $V_6$, $V_3$ and $V_1$ are opened. Similarly, the valve 15v associated with the optical pumping cell 15 is opened (typically the valve 15v is opened upon attachment to the gas flow path 10p and remains open until it is removed from the system 10). This portion of the gas flow path 10p may also be purged and evacuated (using the purge gas source 30 and the vacuum pump 50) to remove oxygen prior to release of the target gas, as needed. As used herein, the term "target gas" means the gas to be polarized and can include pre-formulated gas mixtures that include a suitable amount percentage of the target gas itself, as is known to those of skill in the art.

As the target gas flows downstream of the target gas source 40, the pressure in the gas flow path rises. As the pressure adjacent valve $V_3$ increases to a predefined pressure threshold, as read by the pressure gage PG1, valve $V_3$ closes. This operation pressurizes the optical pumping cell 15c to a desired pressure. The pressurizing/filling procedure can be carried out at ambient temperature. However, the target gas may be pre-heated or heated along the gas flow path 10p, as desired. In certain embodiments, the pressure threshold is about 111 psi. At this point, valves $V_3$ and/or $V_6$ as well as valve $V_1$ may be automatically closed. The control module 12 may direct the closure. The polarization process can then be initiated. When spin exchange with rubidium is the polarization process, the optical pumping cell 15c may be heated and the pressure in the cell increased to about 4-10 atm. The process can take up to about 8 hours, depending on the target gas and protocol used. Subsequent to the polarization process, the cell 15c can be actively cooled or allowed to return to ambient temperature. As the cell 15c returns to ambient temperature or, at a predetermined time in the process, based on other input or predetermined parameters, the dispensing system 10 can be purged and evacuated to prepare it to dispense the hyperpolarized gas. However, it is noted that the dispensing can be carried out before the polarized gas returns to ambient, taking into account the temperature influence on the meted volumes. In any event, allowing the cell to return to below about 40° C. can allow the Rb to settle or self-filter from the polarized gas.

As the time for active dispensing approaches, the system 10 can be directed to automatically purge and evacuate the dispensing pathway to remove oxygen or other contaminants. Typically the purge and evacuation process is carried out less than about 1 hour in advance of the initiation of the active dispensing protocol, typically in less than about 30 minutes, and more typically in less than about 10 minutes in advance of the initiation of the active protocol that initiates the dispensing of the gas. In particular embodiments, the purge and evacuation can be carried out at about 2 minutes or less in advance of the initiation of the active dispensing protocol.

In operation, referring to FIG. 5, valves, $V_1$, $V_4$, and $V_6$ are closed, and valves $V_7$, $V_5$, and $V_2$ are opened (as well as the valve proximate the container 25v). Purge gas from the buffer/purge gas source 30 can be directed to flow downstream and into the container 25. If the container 25 used is a collapsible/inflatable type, the purge gas can be controlled to partially inflate the container 25 so as to inhibit over pressurizing same. The control can be implemented using a pressure gage with a ceiling limit proximate the container 25 and/or by calculating the number of meted space volumes ($V_T$ of either space 20f and/or 20c) needed to fill the container to a default percentage, such as 60% capacity.

In certain embodiments, a user can input the container size 25 prior to active dispensing and/or purge/evacuation as well as other desired formulation data. The system 10 can consider the inputs and then generate the amount of capture and release cycles (and/or the number of fine and/or coarse cycles 20f, 20c, respectively) that will be used to dispense the desired formulation.

Thus, for example, the pressurized filler/purge gas source 30 can operate a known substantially constant pressure, as the pressure gage PG1 reads the threshold amount, such as about 82-86 psi. For a coarse $V_T$ of about 99 cc's and a fine $V_T$ of 3 cc's, five successive coarse space capture and release cycles can be carried out and one capture and release in the fine space 20f can be carried out to output a cumulative dispensed volume of 498 cc's. Because this amount is under the desired amount, the system 10 can also be configured to output two fine meted space volumes to provide a cumulative dispensed volume of 501 cc's. The system 10 can be configured to decide in situ whether to dispense above or below the requested amount, based on acceptable predetermined tolerances, or may allow a user to select the output amount.

Next, valves $V_5$ and $V_7$ can be closed and valve $V_4$ opened to allow the open gas flow path to be evacuated to remove the purge gas and oxygen in these spaces therewith. A vacuum gage (shown as VG) can be used to run this operation until the pressure is about 30-50 millitorr. The purge and evacuation procedure can be automatically repeated a plurality of times, such as two, three, or more. The purge and evacuation can be carried out on the order of a few minutes to less than about an hour, typically less than about 20-30 minutes. The purge and evacuation process can be automatically controlled and/or initiated so that it is complete proximate in time to the completion of the polarization process. The filler/purge gas source 30 is shown as a common source, but separate sources may also be used. One suitable filler/purge gas is medical grade 5 nitrogen, but other suitable purge and/or filler gases or gas mixtures may also, be used that are biocompatible and polarization friendly may also be used.

Thus, at this time, gas flow path 10p used for dispensing to the container 25 is prepared. If the system 10 and/or user has identified that the desired formulation uses a buffer gas(es) and hyperpolarized gas blend, the aliquot of buffer/filler gas is typically dispensed in advance of the hyperpolarized gas. The relevant parameters are identified and the aliquot of each gas or gas mixture to be dispensed can be automatically identified as noted above using pressure, volume relationships and program code that adjusts and determines the amounts at the time of dispensing based on dynamic parameters. Assuming a 1.0 L end cumulative bolus (set by default conditions or user input or the like) and a starting polarization level of 30% on board cell polarization, it may be desirable to provide a polarization concentration of between about 20-50%. Thus, the end dispensed blend formulation is calculated as 500 cc's of buffer/filler gas (such as nitrogen) and 500 cc's of polarized gas.

Figure 8A:
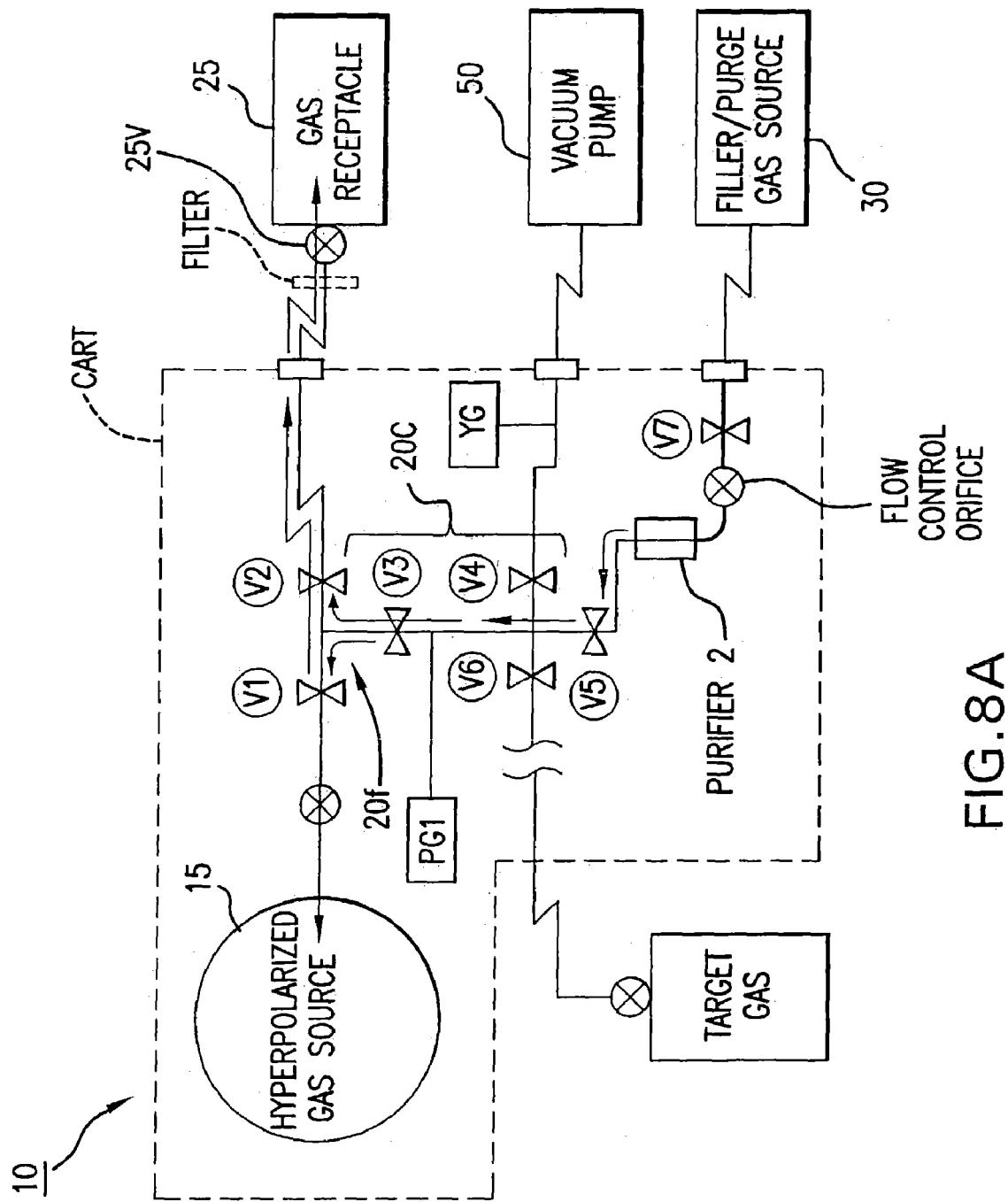
FIG. 8A illustrates a flow path of a buffer and/or purge gas in the system of FIG. 5 according to embodiments of the present invention.

Thus, referring now to FIG. 8A, the filler/purge gas can be released, to be dispensed, through the gas flow path 10p at substantially constant pressure. The flow arrows indicate the general flow direction. In certain embodiments, the buffer/filler gas is released at about 60-90 psi and five capture and release cycles of the coarse meted space volume 20c followed by one capture and release cycle of the small meted space volume 20f. Thus, as shown in FIG. 8A, valves $V_1$ $V_4$ and $V_6$ remain closed during the buffer gas dispensing procedures. Valve $V_2$ is closed, valves $V_7$, $V_5$, and $V_3$ are opened and, when the pressure gage PG1 stabilizes at the desired pressure, $V_3$ or $V_5$ can be closed, depending on whether the larger meted space 20c will be used for the capture and release cycle, or the smaller meted space 20f. Thus, a discrete amount of buffer gas is held, temporarily captured in the automatically selected meted space, either 20c or 20f. Subsequently, valve $V_2$ is opened, with valves $V_1$ and $V_3$ or $V_5$ closed, to release the briefly captured discrete amount of gas to the downstream container 25. The capture and release cycles can be automatically successively rapidly repeated based on the calculated number needed to provide the desired aliquot amount of gas/gas mixture to the container 25.

Figure 8B:
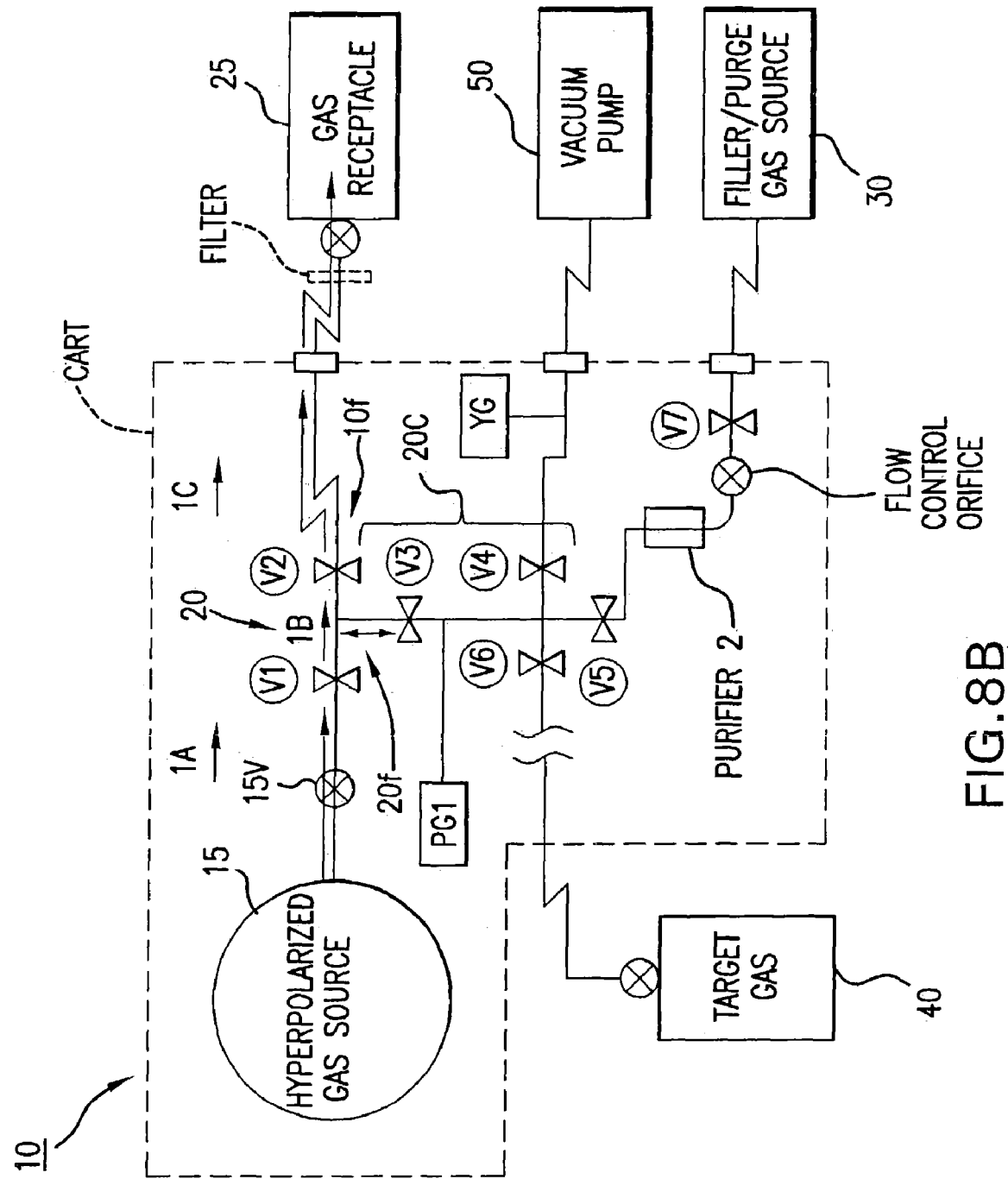
FIG. 8B illustrates a flow path of a hyperpolarized gas using a first meted volume space according to embodiments of the present invention.
Figure 8C:
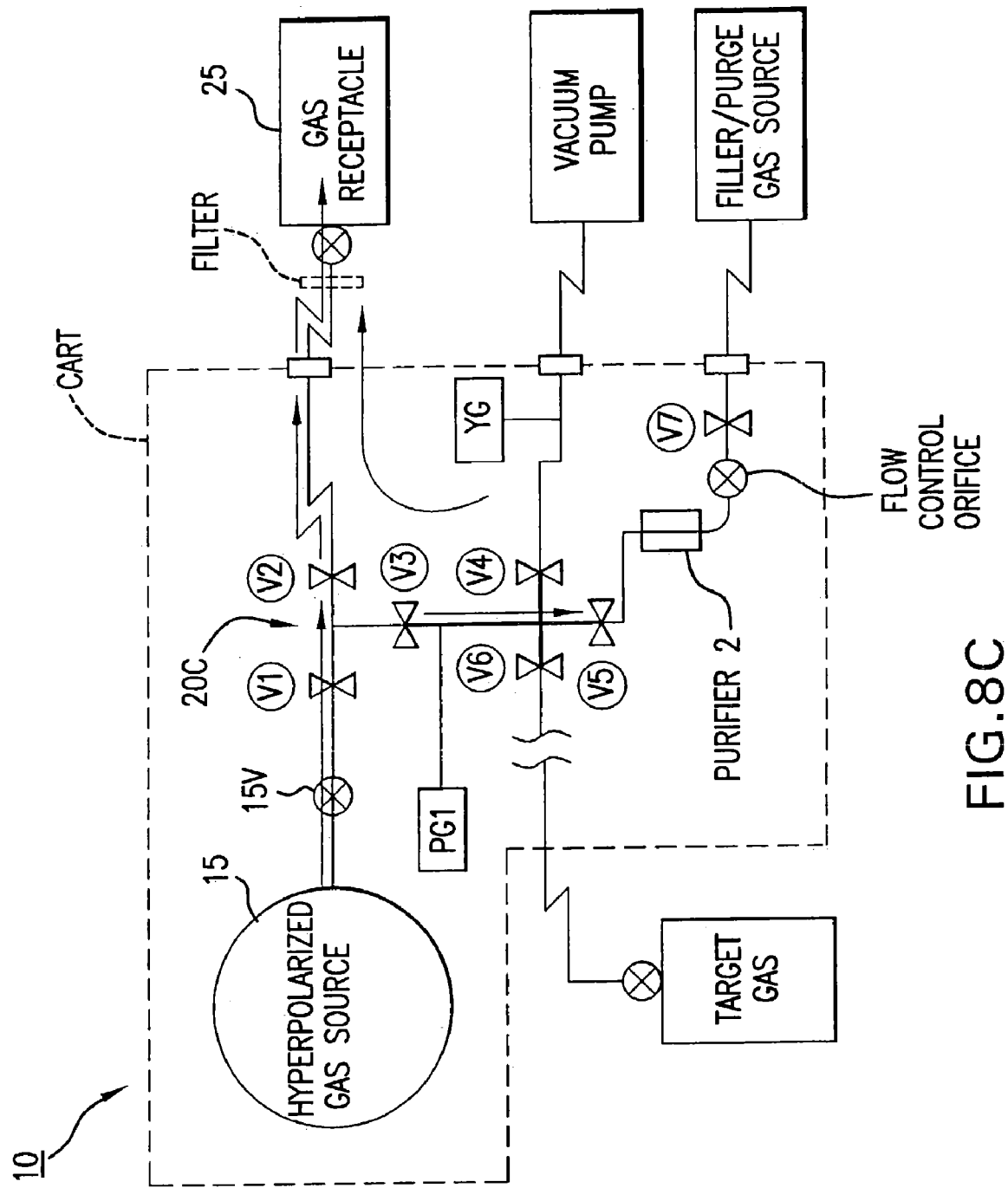
FIG. 8C shows the diagram of FIG. 5 and illustrates a flow path of a hyperpolarized gas using a second meted volume space in the system of FIG. 5 according to embodiments of the present invention.

As shown in FIGS. 8B and 8C, to initiate hyperpolarized gas dispensing, valves $V_1$, $V_5$ and $V_7$ are closed. Valve $V_2$ is then closed and valves $V_3$ and/or $V_5$ is closed, depending on whether the fine meted volume 20f (FIG. 8B) or coarse meted volume 20c (FIG. 8C) is selected. Valve $V_1$ is opened (with valves $V_2$ and $V_3$ and/or $V_5$ closed) and then closed to temporally or temporarily allow gas to flow downstream and be captured as a discrete amount of hyperpolarized gas in the meted space 20. Valve $V_2$ is opened to release the briefly captured discrete amount of gas, which then flows downstream to the dispensing container 25 as shown by the flow arrows. The operations are successively rapidly repeated to provide the desired aliquot amount of hyperpolarized gas to the container 25. As shown in FIG. 8B, the flow sequence is illustrated by element numbers 1A, 1B, and 1C. Sequence 1A represents that the gas is released and enters the meted space 20 (shown as the fine space 20f). Sequence 1B illustrates that the discrete amount of gas is captured when the intermediate flow path (shown as a "T" space) termed the meted space 20 is selectively automatically isolated briefly from the remainder of the flow path 10p. Sequence 1C illustrates that the captured gas is then released and travels downstream to the container 25. The container 25 is then filled with the bolus formulation, which may be a pharmaceutical grade product suitable for in vivo administration. For multi-bolus hyperpolarized gas sources, the process can be repeated, with a new $P_0$ determined and a new polarization level established for the remaining quantity of hyperpolarized gas. The system 10 can then automatically reinitiate the dispensing protocol to dynamically adjust and/or calculate the aliquots needed to provide the next desired formulation parameters (which can be automatically varied from the prior dispensed quantities or formulations) for the subsequent bolus and to determine the number of capture and release cycles for each of the gases/mixtures to be meted to the next container 25.

The pressure differential in the gas flow path 10p during the dispensing operations directs the gas to flow downstream to the container 25, which is typically held at atmospheric pressure. The container 25 may be held at other pressures sufficient to induce downstream flow suitable for dispensing.

The optical pumping cell 15c has an associated known volume and pressure and is filled with a plurality of bolus or aliquot of hyperpolarized gas. The system 10 may also be configured to dispense a single aliquot from the hyperpolarized gas source (the hyperpolarized gas source may be sized as a single bolus container). The volume $V_T$ defined by the first or second meted spaces 20f, 20c, respectively is known. At initiation of the dispensing protocol, a pressure reading can be obtained, such as by using the PG1 pressure sensor, to determine the starting pressure $P_0$ in the cell or hyperpolarized gas source 15. In certain embodiments, the pressure reached at the time of filling of the optical cell with target gas is assumed to be the starting pressure $P_0$. This inhibits or reduces the hyperpolarized gas contact time with the gage during active dispensing which can improve the polarization level in the container 25.

Thus, for the embodiment shown in FIG. 8B, valves $V_2$, $V_5$, and $V_6$ remain closed and valve $V_3$ and $V_1$ are opened (or the pressure gage can be repositioned in the meted space 20 to allow valve $V_3$ to remain closed). In addition, the pressure gage PG1 may be positioned in fluid communication with the gas flow path 10$p$ but located outside both the fine and coarse meted spaces 20$f$, 20$c$. In any event, after stabilization, typically prior to polarization, the pressure reading can be obtained. Typically, for a filling pressure of 110 psi, the starting pressure at dispensing of the hyperpolarized gas will be between 109-111 psi. Other pressures may be used as discussed above. In normal operation of the active dispensing procedure that emits the aliquots of hyperpolarized gas into the container, valves $V_1$ and $V_2$ are not open at the same time.

Figure 9:
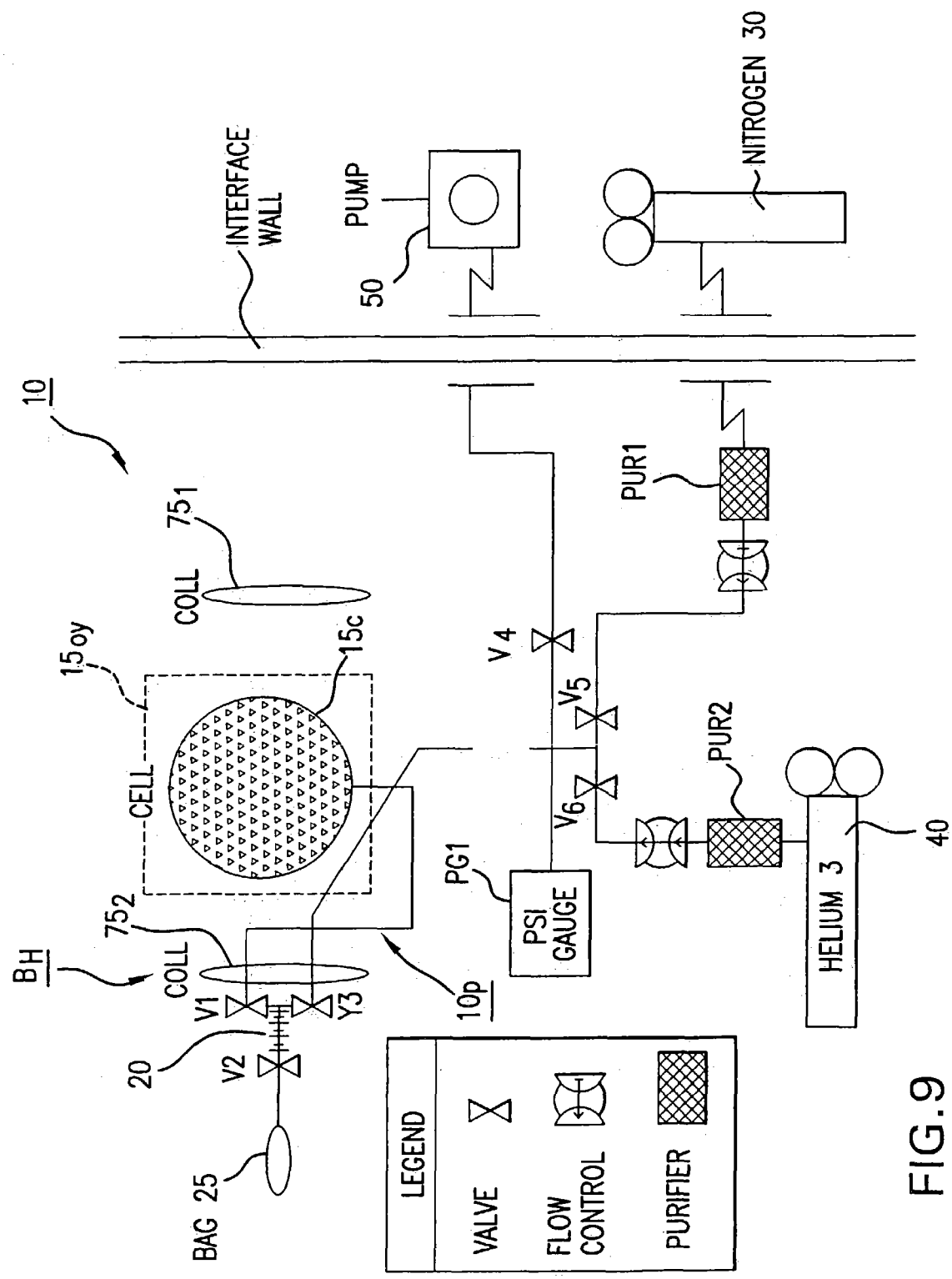
FIG. 9 is a schematic illustration of a hyperpolarized gas dispensing system according to particular embodiments of the present invention.

FIG. 9 illustrates that the system 10 can be configured to generate a magnetic holding field $B_H$ that provides a region of magnetic homogeneity about the optical pumping cell 15$c$ and the container 25 as well as portions of the gas flow path 10$p$, particularly the portion that distributes or dispenses the hyperpolarized gas. In the embodiment shown, an axially dispersed magnetic holding field $B_H$ can be generated so that it covers the gas dispensing region of the gas flow path 10$p$, including the meted space 20 defined by the portion of the flow path 10$p$ intermediate valves $V_1$-$V_3$. As shown, the holding field $B_H$ may be provided by two spaced apart Helmholtz coils $75_1$, $75_2$. Solenoid designs may also be used such as those described in U.S. Pat. No. 6,269,648, the contents of which are hereby incorporated by reference as if recited in full herein. The polarized gas can be dispensed from the optical cell by directing the gas to flow or dispense along the axis of the solenoid. The homogeneous magnetic field may be configured to provide about dB/B of less than about 0.001 cm$^{-1}$ for those portions of the system 10 where polarized gas will reside for any substantial length of time, such as above about 30 minutes to 1 hour or more, like in the main body of the optical pumping cell 15$c$ itself. In other portions of the system, such as where the polarized gas will be flowing, but not sitting for any substantial length of time, a homogeneity of less than about 0.01 cm−1 may be sufficient for pumping and/or dispensing. In addition, two or more separate holding fields may be employed to generate the desired homogeneity and field strength over the appropriate portions of the gas flow dispensing system 10.

In certain embodiments such as the embodiment shown in FIG. 9, for a dispensing system 10 with an on-board or integrated hyperpolarizer unit and a magnetic field $B_H$ generated by "on-board" 6-19 inch diameter Helmholtz coils, the coils may be positioned and configured to generate a region of homogeneity which is defined by a virtual cylinder having a length of less than about 2 inches and a radius of less than about 2 inches centered between the coils (with the optical cell 15$c$ being located in the homogeneous region created thereby). The relatively small center area described is the region where the polarization reading can be obtained. In certain embodiments, the region of homogeneity can be expanded so as to extend out from the center effectively protecting the polarized gas from significant polarization loss. In particular embodiments, the homogeneity of the field may extend further along the axis of the coils, and positioning the valves in the axial extension can allow the valves to perform axially dispensing in a protected region, thereby inhibiting polarization losses associated therewith.

Where electromagnetic solenoids are used, they may be configured as an end compensated solenoid to flatten out and extend the homogeneous field as described in U.S. Pat. No. 6,269,648 incorporated by reference above (not shown herein). The solenoid can provide increased regions or volumes of homogeneity or that conventionally provided by Helmholtz coils. In certain embodiments, the solenoid can be sized and configured with about a 10-12 inch diameter. The cylindrical solenoid may also be configured to be about 20-60 inches long or even longer, and typically can be about 40 inches long.

In operation, when obtaining polarimetry measurements of the polarized gas, the oven temperature can be measured or obtained (based on known controlled operation) because at high temperatures the gas density will be reduced according to the relationship expressed by the ideal gas law (PV=nRT). For example, if the oven 15$ov$ is set to operate at 150° C., the density of xenon is about (295K/423K or 0.70) of the room temperature density. The signal associated with the hyperpolarized gas when measured at room temperature versus greatly elevated temperatures can be reduced correspondingly.

Figure 11:
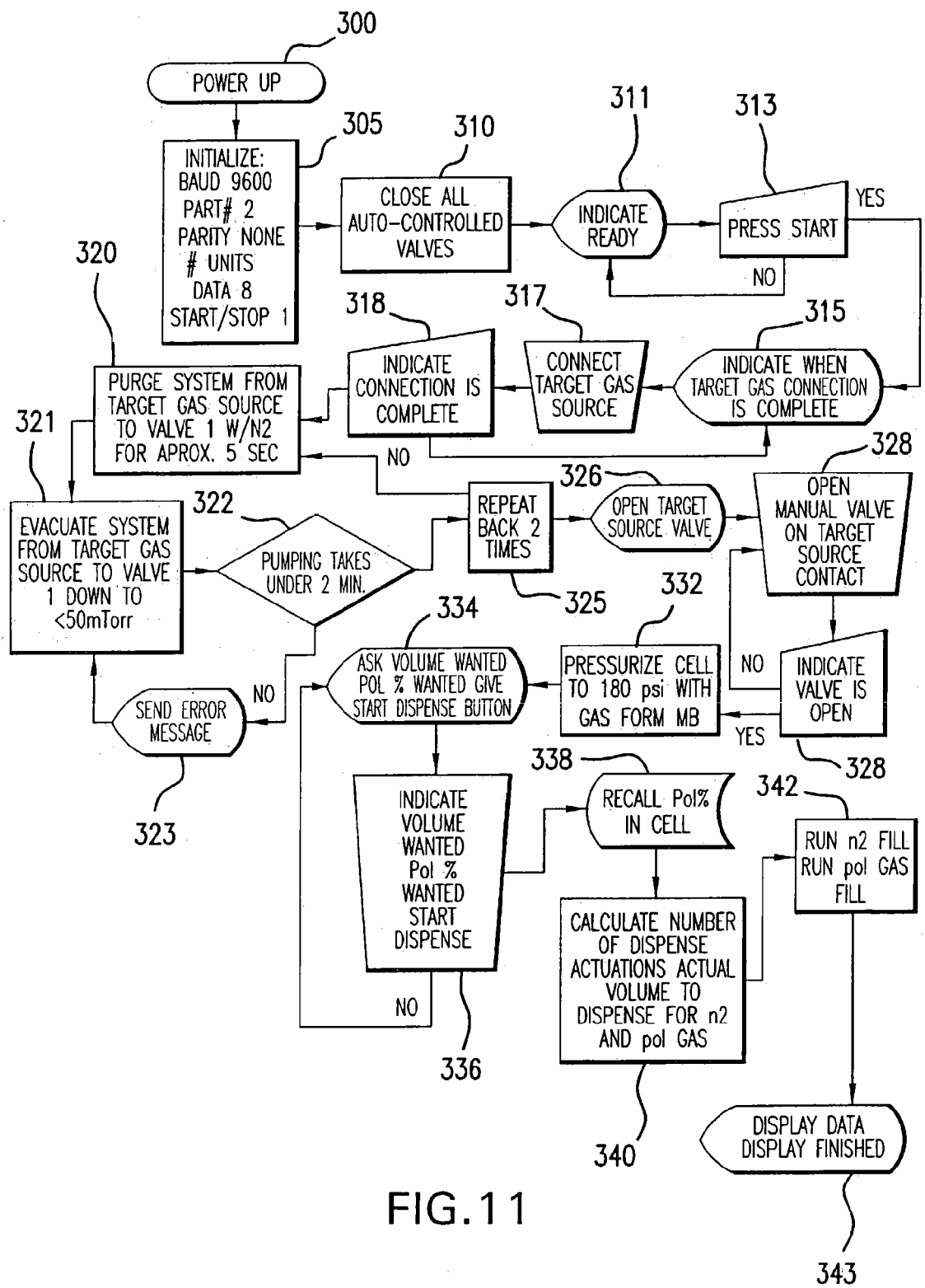
FIG. 11 is a flow chart suitable for carrying out operations according to embodiments of the present invention.

Turning now to FIG. 11, another set of operations that may be used to carry out embodiments of the invention is illustrated. The system can be powered up (block 300) and initialized by setting the ports and the communications modem initialized (block 305). The modem or communication system may be set to run at a desired baud rate (shown as 9600) and with the desired port, parity, and number of data bits to be used. All automatically controlled valves can be closed (block 310). The system can be monitored for certain operational parameters and, when the system indicates all is ready (block 311), an activation or start (block 313) can be selected by a user or automatically. Once start has been indicated, the system can monitor to determine when the connection to the target gas source is complete (block 315); if no target gas source is found, or a misalignment or under pressure condition is sensed, an alert or notice can be rendered so that a user can connect (block 317) (or tighten or correct the connection) the target gas source or replace with a new target gas source. When the connection is complete, the system is notified (block 318). The appropriate valves are selectively opened and others closed and the purge and evacuate process can then be started. As shown, the system can be purged from the target gas source to value $V_1$ with a purge gas such as nitrogen for about 5 seconds (block 320) and then this portion of the system can be evacuated down to less than about 50 mTorr (block 321). The evacuation pumping process can be carried out in less than about 2 minutes (block 322); if the pressure fails to reduce to the desired level within this time, an error message can be generated (block 323). The operations in blocks 320-322 can be repeated two or more times (block 325). The target source container valve can be opened (block 326). For manual valves, the system can send instructions to the user to manually open the target source container valve (block 328) and to indicate when this task is completed (valve open) (block 330). When open, the optical pumping cell can be pressurized to about 180 psi with gas from the target gas source (block 332). The purge and evacuation protocol can be run for the system from the buffer/filler gas source to the container. Either upon activation of the system or just prior to active dispensing, the system can request entry from a user regarding the percent polarization wanted in the end volume of the first (bolus) product formulation desired, and allow the user to start the active dispensing (as well as subsequent boli) (block 334). The system can prod for the input parameters if not received by the user (block 336). The polarization level in the cell can be recalled (block 338) and the number of dispense actuations to be used to yield the actual volume desired for both nitrogen (buffer/filler gas) as well as the hyperpolarized gas (block 340). The system can automatically serially run the nitrogen or filler gas dispensing procedure and the polarized gas dispensing procedure (block 342). The cumulative volume, percent polarization concentration and preparation date can be displayed (block 343).

Figure 12:
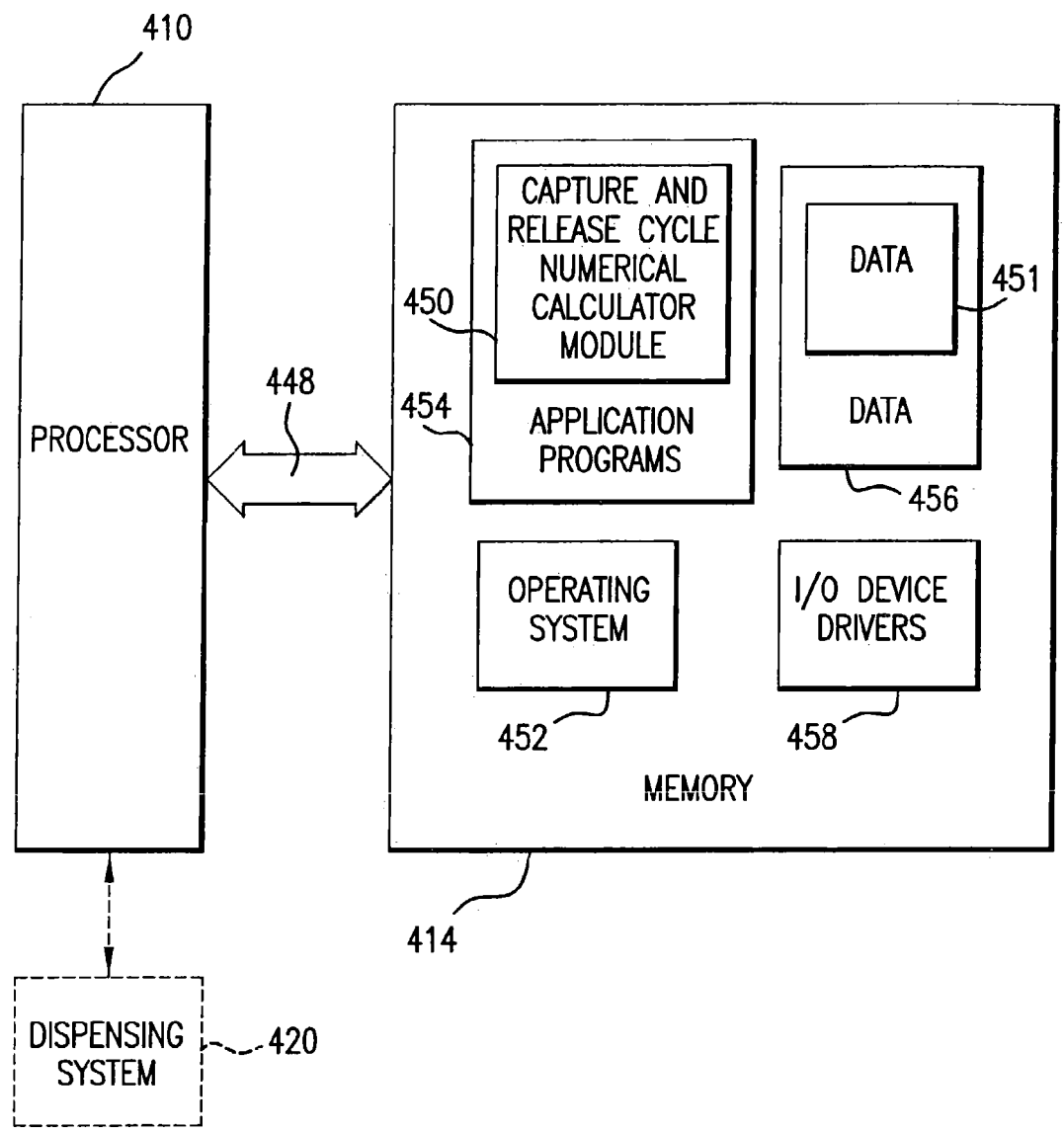
FIG. 12 is a schematic diagram of a computer program module according to embodiments of the present invention.

FIG. 12 is a block diagram of exemplary embodiments of data processing systems that illustrates systems, methods, and computer program products in accordance with embodiments of the present invention. The processor 410 communicates with the memory 414 via an address/data bus 448. The processor 410 can be any commercially available or custom microprocessor. The memory 314 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 12, the memory 414 may include several categories of software and data used in the data processing system 405: the operating system 452; the application programs 454; the input/output (I/O) device drivers 458; the successive capture and release cycles calculation module 450; and the data 456. The data 456 may include pressure and/or polarization level data 451 which may be obtained from the dispensing or hyperpolarization system 420. As will be appreciated by those of skill in the art, the operating system 452 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the dispensing system 420. The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the capture and release cycle calculation module 450 being an application program in FIG. 12, as will be appreciated by those of skill in the art, other configurations may also be utilized while still benefiting from the teachings of the present invention. For example, the module 450 may also be incorporated into the operating system 452, the I/O device drivers 458 or other such logical division of the data processing system 405. Thus, the present invention should not be construed as limited to the configuration of FIG. 12, which is intended to encompass any configuration capable of carrying out the operations described herein.

In certain embodiments, the capture and release calculation module 450 includes computer program code for automatically determining the number of fine and/or coarse capture and release cycles to be used and successively directing the selective operation of the valves in the gas flow path accordingly.

The I/O data port can be used to transfer information between the data processing system 405 and the dispensing system 420 or another computer system or a network (e.g., the Internet) or to other devices controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 12 but is intended to encompass any configuration capable of carrying out the operations described herein.

The flowcharts and block diagrams of certain of the figures herein illustrate the architecture, functionality, and operation of possible implementations of meted dispensing means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the system 10 can accept user input regarding the number of procedures, the type of procedure scheduled and the days and times of the scheduled appointments over a selected period of time. The user input may indicate whether the planned procedure is for NMR or MRI evaluation (or both). For example, the scheduled procedure can be correlated to the quantity and type of polarized gas or gas formulation that is needed to support the procedure. This may include one or both injected or inhaled formulations and quantities, and the amount may depend on whether the procedure will be for ventilation (typically static), dynamic imaging or signal analysis, oxygen diffusion/perfusion mapping, dynamic with oxygen mapping or perfusion. The procedure can also indicate the targeted region to be evaluated, such as, but not limited to, the pulmonary system, the cardio-pulmonary system, the cerebrum or brain, or another other Organ, system, or region of interest. Information regarding the scheduled procedure can be used to generate an estimated associated polarized gas amount and type needed to support the planned evaluation which can be used to determine the appropriate automatically operated dispensing protocol.

The polarization can be carried out in a "just-in-time" format, or so that limited storage (typically within about 24-72 hours of dispensing) of the polarized gas is required. Longer storage times can be used in certain applications. However, both polarized $^{129}$Xe and $^{3}$He have a limited clinically useful polarization life. The polarization life depends on a number of factors, including surface-induced relaxation mechanism. For example, the collisions of gaseous $^{129}$Xe and $^3$He with container walls ("surface relaxation") have historically been thought to dominate most relaxation processes. Another relaxation mechanism is the relaxation due to EMI and oscillating magnetic fields. Unfortunately, EMI can be generated by relatively common sources; as such, transport away from the hyperpolarized gas production site can expose the hyperpolarized gas to these undesirable relaxation sources which, in turn, can dramatically reduce the polarization life of the transported gas (i.e., the $T_1$). For example, EMI is typically generated from a vehicle's engine, high voltage lines, power stations and other current carrying entities. Still another relaxation mechanism is magnetic gradient relaxation that involves the relaxation attributed to the exposure of the hyperpolarized noble gases to inhomogeneous static magnetic fields. Generally stated, as the polarized gas atoms diffuse or move through an inhomogeneous magnetic field, they experience a time-dependent field, which can introduce depolarizing activity onto the hyperpolarized atoms. See U.S. Pat. No. 6,269,648 (the contents of which are hereby incorporated by reference as if recited in full herein) for additional description of relaxation mechanisms and for a description of shielded transport and storage containers or chambers.

As noted above, the container 25 may be a collapsible bag sized so that the pre-packaged amount of unpolarized gas does not completely fill the capacity and, instead, only partially fills the volumetric capacity thereof. For example, filling to about 30-60% capacity may provide a suitable expansion factor. This can allow for expansion of the gas during transport at increased altitudes or other environmental or shipping conditions.

Generally stated, where on-board spin-exchange polarization is employed, an optical pumping source, such as a light source such as a laser (i.e., a diode laser array) can be directed into the optical pumping cell 15c (FIGS. 7 and 9) through various focusing and light distributing means, such as lenses, mirrors, and the like (not shown). In certain embodiments, the laser is circularly polarized to optically pump alkali metal held in the cell. As shown by FIG. 9, the cell 15c can be positioned inside a temperature-regulated oven 15ov (illustrated by a broken line). The temperature during polarization may be between 170-200° C.

Generally described, the optical pumping cell is configured to polarize noble gas via spin-exchange. The unpolarized pre-mixed target gas mixture is introduced into the polarizer optical pumping cell 15c. The polarization process can be relatively lengthy, depending on the type of gas and amount of polarized gas desired. For example, a typical $^3$He polarization time of typical single or multi-dose batch amounts can be from about 1 hour-8 hours, while $^{129}$Xe may be configured to produce a single patient dose of about 1 liter in about 1-3 hours and typically in under about 60-90 minutes.

For $^{129}$Xe "continuous" flow based polarization, the typical residence time of the gas in the cell 15c is about 10-30 seconds; i.e., it takes on the order of 10-30 seconds for the gas mixture to be hyperpolarized while moving through the cell 15c. The polarizer cell 15c can be a high-pressure spherical high-purity aluminosilicate optical pumping cell (or aluminosilicate coated cell) and the like. During operation, the oven 15ov defines a heated chamber with apertures configured to allow entry of the laser-emitted light into the optical pumping cell 15c. A vaporized alkali metal such as Rb is introduced into the polarizer cell 15c. Typically the alkali metal is put in the cell prior to initiation of the polarization process. The Rb vapor is optically pumped via the optic light source.

The optical cell can also employ helium as an additive-gas to pressure broaden the Rb vapor absorption bandwidth. The selection of a buffer gas can be important because the buffer gas—while broadening the absorption bandwidth—can also undesirably impact the alkali metal-noble gas spin-exchange by potentially introducing an angular momentum loss of the alkali metal to the buffer gas rather than to the noble gas as desired.

As will be appreciated by those of skill in the art, Rb is reactive with $H_2O$. Therefore, any water or water vapor introduced into the optical cell 15c can cause the Rb to lose laser absorption and decrease the amount or efficiency of the spin-exchange in the optical cell 15c. Thus, as an additional precaution, an extra filter or purifier can be positioned before the inlet of the optical cell 15c with extra surface area to remove even additional amounts of this undesirable impurity in order to further increase the efficiency of the hyperpolarizer 10.

Cooling means to cool the cell to ambient temperature can be used to precipitate the alkali metal from the polarized gas stream. In other embodiments, heat to the Oven 15ov is turned off and natural cooling is used to condense the Rb out of the vapor phase and collect it in the bottom of the optical pumping cell 15c. In addition, a micro-pore filter can be used. As will be appreciated by one of skill in the art, the alkali metal can precipitate out of the gas stream at temperatures of about 40° C. Other filtering means can also be used, such as, but not limited to, an alkali metal reflux condenser (not shown). The refluxing condenser employs a vertical refluxing outlet pipe that can be kept at room temperature. The gas flow velocity through the refluxing pipe and the size of the refluxing outlet pipe is such that the alkali metal vapor condenses and drips back into the pumping cell by gravitational force. In any event, it is desirable to remove alkali metal prior to delivering polarized gas to a patient to provide a non-toxic, sterile, or pharmaceutically acceptable substance (i.e., one that is suitable for in vivo administration).

Typically, the polarized $^{129}$Xe is then accumulated in a cold finger where it is frozen and subsequently thawed to provide the polarized $^{129}$Xe that can be dispensed into the container 25. Additional description of suitable polarizers and cold fingers is included in U.S. Pat. Nos. 5,642,625, 5,809,801, and 6,709,213, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A computer program product for operating a hyperpolarized gas dispensing system having a gas flow path with a plurality of spaced apart remote-controlled actuated valves that open and close to direct the flow of gas therein and to close off at least one intermediate portion of the gas flow path having a known volume, the computer program product comprising:
   a computer readable storage medium having computer readable program code embodied in said medium, said computer-readable program code comprising:
   computer readable program code that obtains the pressure of a pressurized hyperpolarized gas source;
   computer readable program code that obtains the polarization level of the hyperpolarized gas held in the hyperpolarized gas source;
   computer readable program code the receives input about the desired formulation of hyperpolarized product, including at least one of: the target bolus volume; the desired bolus polarization level percentage or concentration; the type of gas(es) to be dispensed to form the bolus; and the size and/or type of the bolus container;
   computer readable program code that calculates the amount of hyperpolarized gas needed to produce the desired bolus formulation;
   computer readable program code that calculates the number of capture and release actuations of predetermined ones of the actuated valves needed to dispense the calculated amount; and
   computer readable program code that automatically transmits control signals to the predetermined ones of the remote actuated valves during operation of the dispensing system to cause selected valves to open and/or close at appropriate times so as to selectively temporarily close off a predetermined intermediate portion of the gas flow path having a known volume from the remainder of the gas flow path to capture a discrete amount of gas therein and to then rapidly open to release the captured discrete amount of gas therefrom.

2. A computer program product according to claim 1, further comprising computer readable program code that dynamically considers, and adjusts as needed, the aliquot amount of hyperpolarized gas needed to produce the desired bolus formulation for each successive dispensed bolus; and
   computer readable program code that re-calculates the number of capture and release actuations of predetermined ones of the actuated valves needed to dispense the calculated aliquot amount of hyperpolarized gas bolus to bolus.

3. A computer program product according to claim 1, further comprising computer readable program code that determines the amount of buffer gas needed to produce the desired bolus formulation;
   computer readable program code that calculates the number of capture and release actuations of predetermined ones of the actuated valves needed to dispense the calculated amount of the buffer gas; and
   computer readable program code that initiates the actuation of the valves to dispense the buffer gas in advance of the hyperpolarized gas.

4. A computer program product according to claim 1, further comprising computer readable program code for using the universal pressure relationship, the volume of the closed intermediate portion of the gas flow path, and the pressure of the pressurized source of hyperpolarized gas and buffer gas to determine the number of actuations and valves needed to dispense the desired aliquot amounts of buffer gas and hyperpolarized gas.

5. A computer program product according to claim 1, further comprising computer program code for initiating a purge and evacuation of the gas flow path in advance of the dispensing of the buffer and hyperpolarized gases.

6. A computer program product for operating a hyperpolarized gas dispensing system having a source of hyperpolarized gas, a source of buffer gas, a gas flow path with a plurality of spaced apart remote-controlled actuated valves that open and close to direct the flow of the hyperpolarized gas and the buffer gas therein and to close off at least one intermediate portion of the gas flow path having a known volume, the at least one intermediate portion being in selectable communication with the sources of hyperpolarized gas and buffer gas, the computer program product comprising:
   a computer readable storage medium having computer readable program code embodied in said medium, said computer-readable program code comprising:
   computer readable program code that automatically transmits control signals to predetermined ones of the remote actuated valves during operation of the dispensing system to cause selected valves to open and/or close at appropriate times so as to selectively temporarily close off the at least one predetermined intermediate portion of the gas flow path having a known volume from the remainder of the gas flow path to capture a discrete amount of the hyperpolarized gas or the buffer gas therein and to then rapidly open to release the captured discrete amount of hyperpolarized gas or buffer gas therefrom;
   wherein the at least one predetermined intermediate portion comprises individually selectable first and second intermediate portions having different first and second associated volumes, respectively, the computer program product further comprising computer readable program code that automatically determines and selects the appropriate combination of the first and second intermediate portions to output the desired aliquot amounts of buffer and hyperpolarized gas; and
   further comprising computer program code that dynamically calculates, and adjusts as needed, the aliquot amount of hyperpolarized gas needed to produce the desired bolus formulation for each successive dispensed bolus; and
   computer readable program code that re-calculates the number of capture and release actuations of valves needed to dispense the calculated aliquot amount of hyperpolarized gas bolus to bolus.

7. A computer program product for operating a hyperpolarized gas dispensing system having a gas flow path with a plurality of spaced apart remote-controlled actuated valves that open and close to direct the flow of gas therein and to close off at least one intermediate portion of the gas flow path having a known volume, the computer program product comprising:
   a computer readable storage medium having computer readable program code embodied in said medium, said computer-readable program code comprising:
   a capture and release cycle calculation module that calculates the number of valve actuation cycles needed to output a desired aliquot of polarized gas.

8. A computer program product according to claim 7, further comprising computer program code that obtains data corresponding to the polarization level of a hyperpolarized gas source; and computer program code that obtains data corresponding to the pressure of a portion of the gas flow path, and wherein the capture and release calculation module considers the polarization and pressure data to determine the number of capture and release cycles.

9. A computer program product according to claim 8, wherein the capture and release cycle calculation module selects the number of cycles to successively isolate one or more of a fine meted space and/or a coarse meted space in the gas flow path to yield the desired aliquot amount of gas being dispensed.

10. A computer program product according to claim 8, wherein the capture and release cycle calculation module selects the number of cycles used to successively isolate one or more of a fine meted space and/or a coarse meted space in the gas flow path to yield the desired aliquot amount of both a non-polarized filler gas and the hyperpolarized gas.

* * * * *